(12) United States Patent
Gilbert et al.

(10) Patent No.: US 7,211,442 B2
(45) Date of Patent: May 1, 2007

(54) MICROFLUIDIC SYSTEM INCLUDING A VIRTUAL WALL FLUID INTERFACE PORT FOR INTERFACING FLUIDS WITH THE MICROFLUIDIC SYSTEM

(75) Inventors: John R. Gilbert, Brookline, MA (US); Nghia Hung Chiem, San Francisco, CA (US)

(73) Assignee: Cytonome, Inc., Boston, MA (US)

( * ) Notice: Subject to any disclaimer, the term of this patent is extended or adjusted under 35 U.S.C. 154(b) by 374 days.

(21) Appl. No.: 10/607,287

(22) Filed: Jun. 25, 2003

(65) Prior Publication Data

US 2004/0091398 A1 May 13, 2004

Related U.S. Application Data

(63) Continuation-in-part of application No. 10/028,852, filed on Dec. 21, 2001.

(60) Provisional application No. 60/391,872, filed on Jun. 25, 2002, provisional application No. 60/299,515, filed on Jun. 20, 2001.

(51) Int. Cl.
  *G01N 1/18* (2006.01)
  *G01N 1/10* (2006.01)
  *G01N 33/566* (2006.01)
  *G01N 35/00* (2006.01)
  *G01N 15/06* (2006.01)

(52) U.S. Cl. ............... 436/177; 43/43; 43/52; 43/53; 43/63; 43/174; 43/177; 43/180; 43/501; 422/50; 422/68.1; 422/100; 422/101; 422/102; 422/103; 422/104

(58) Field of Classification Search .......... 422/50, 422/68.1, 100–104; 436/43, 52, 53, 63, 174, 436/177, 180, 501
See application file for complete search history.

(56) References Cited

U.S. PATENT DOCUMENTS

| 5,429,734 A | 7/1995 | Gajar et al. |
| 5,529,465 A | 6/1996 | Zengerle et al. |
| 5,730,187 A | 3/1998 | Howitz et al. |

(Continued)

FOREIGN PATENT DOCUMENTS

WO  WO 96/04547 A1  2/1996

(Continued)

OTHER PUBLICATIONS

Haswell, S.J., "Development and Operating Characteristics of Micro Flow Injection Analysis Systems Based on Electroosmotic Flow," Analyst. Jan. 1997; 122:1R-10R.

(Continued)

*Primary Examiner*—Jill Warden
*Assistant Examiner*—Brian Sines
(74) *Attorney, Agent, or Firm*—Lahive & Cockfield, LLP; Elizabeth A. Hanley, Esq.; David R. Burns, Esq.

(57) ABSTRACT

A fluid interface port in a microfluidic system and a method of forming the fluid interface port is provided. The fluid interface port comprises an opening formed in the side wall of a microchannel sized and dimensioned to form a virtual wall when the microchannel is filled with a first liquid. The fluid interface port is utilized to perform a labeling operation on a sample.

13 Claims, 19 Drawing Sheets

U.S. PATENT DOCUMENTS

| | | | |
|---|---|---|---|
| 5,757,482 A | 5/1998 | Fuchs et al. |
| 5,779,868 A | 7/1998 | Parce et al. |
| 5,800,690 A | 9/1998 | Chow et al. |
| 5,842,787 A | 12/1998 | Kopf-Sill et al. |
| 5,858,195 A | 1/1999 | Ramsey |
| 5,858,804 A | 1/1999 | Zanzucchi et al. |
| 5,880,071 A | 3/1999 | Parce et al. |
| 5,922,591 A | 7/1999 | Anderson et al. |
| 5,957,579 A | 9/1999 | Kopf-Sill et al. |
| 5,958,202 A | 9/1999 | Regnier et al. |
| 5,971,158 A | 10/1999 | Yager et al. |
| 6,001,229 A | 12/1999 | Ramsey |
| 6,001,231 A | 12/1999 | Kopf-Sill |
| 6,010,607 A | 1/2000 | Ramsey |
| 6,010,608 A | 1/2000 | Ramsey |
| 6,033,546 A | 3/2000 | Ramsey |
| 6,042,709 A | 3/2000 | Parce et al. |
| 6,062,261 A | 5/2000 | Jacobson et al. |
| 6,068,751 A | 5/2000 | Neukermans |
| 6,080,295 A | 6/2000 | Parce et al. |
| 6,086,825 A | 7/2000 | Sundberg et al. |
| 6,090,251 A | 7/2000 | Sundberg et al. |
| 6,106,685 A | 8/2000 | McBride et al. |
| 6,110,332 A | 8/2000 | Swierkowski |
| 6,110,343 A | 8/2000 | Ramsey et al. |
| 6,120,666 A | 9/2000 | Jacobson et al. |
| 6,130,098 A | 10/2000 | Handique et al. |
| 6,143,152 A | 11/2000 | Simpson et al. |
| 6,150,119 A | 11/2000 | Kopf-Sill et al. |
| 6,167,910 B1 | 1/2001 | Chow |
| 6,186,660 B1 | 2/2001 | Kopf-Sill et al. |
| 6,192,768 B1 | 2/2001 | Wallman et al. |
| 6,193,471 B1 | 2/2001 | Paul |
| 6,197,595 B1 | 3/2001 | Anderson et al. |
| 6,213,151 B1 | 4/2001 | Jacobson et al. |
| 6,221,226 B1 | 4/2001 | Kopf-Sill |
| 6,221,677 B1 | 4/2001 | Wu et al. |
| 6,231,737 B1 | 5/2001 | Ramsey et al. |
| 6,251,343 B1 | 6/2001 | Dubrow et al. |
| 6,271,038 B1 | 8/2001 | Liu et al. |
| 6,274,089 B1 | 8/2001 | Chow et al. |
| 6,284,113 B1 | 9/2001 | Bjornson et al. |
| 6,290,909 B1 | 9/2001 | Paul et al. |
| 6,296,020 B1 | 10/2001 | McNeely et al. |
| 6,342,142 B1 | 1/2002 | Ramsey |
| 6,376,181 B2 | 4/2002 | Ramsey et al. |
| 6,399,396 B1 | 6/2002 | Bass |
| 6,409,900 B1 | 6/2002 | Parce et al. |
| 6,416,642 B1 | 7/2002 | Alajoki et al. |
| 2001/0051334 A1 | 12/2001 | Barth et al. |

FOREIGN PATENT DOCUMENTS

| | | |
|---|---|---|
| WO | WO 99/15876 A1 | 4/1999 |
| WO | WO 00/58724 A1 | 10/2000 |
| WO | WO 01/59440 A3 | 8/2001 |

OTHER PUBLICATIONS

Onnerfjord P, Nilsson J, Wallman L, Laurell T, Marko-Varga G. Picoliter sample preparation in MALDI-TOF MS using a micromachined silicon flow-through dispenser. Anal Chem. Nov. 15, 1998;70(22):4755-60.

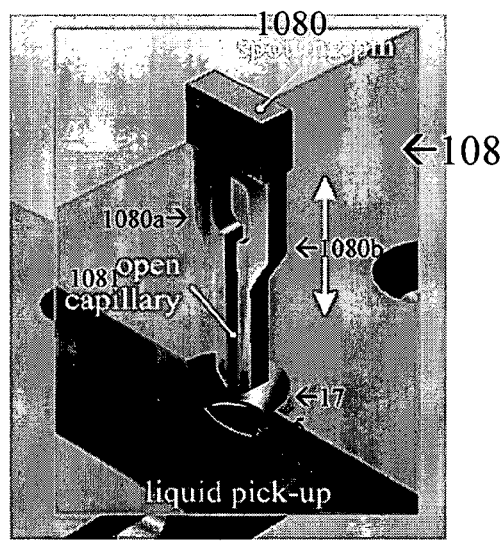
FIGURE 12G
FIGURE 12E      FIGURE 12F
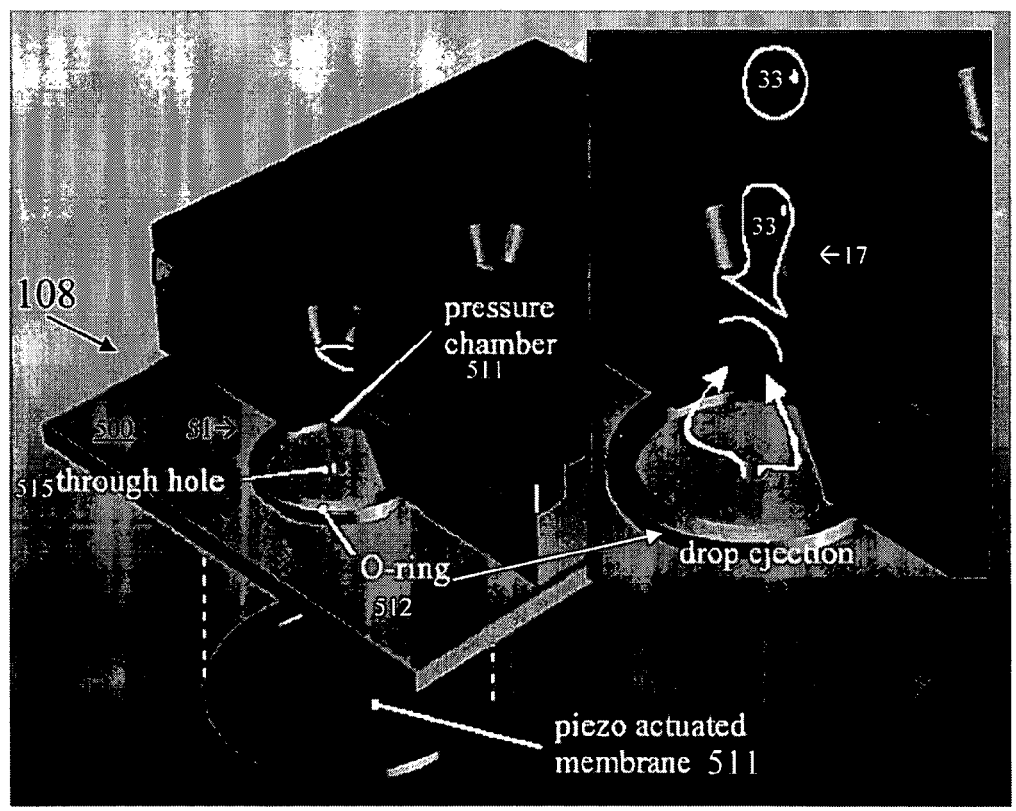

MICROFLUIDIC SYSTEM INCLUDING A VIRTUAL WALL FLUID INTERFACE PORT FOR INTERFACING FLUIDS WITH THE MICROFLUIDIC SYSTEM

RELATED APPLICATIONS

The present application is a continuation-in-part of U.S. patent application Ser. No. 10/028,852, filed Dec. 21, 2001 and entitled Microfluidic System Including a Virtual Wall Fluid Interface Port for Interfacing Fluids With the Microfluidic System, the contents of which are herein incorporated by reference. The present application also claims priority to U.S. Provisional Patent Application Ser. No. 60/391,872, filed Jun. 25, 2002 and entitled Microfluidic Chip with Post-Column Labeling, the contents of which are herein incorporated by reference.

FIELD OF THE INVENTION

The present invention relates to fluidic interface ports for providing bi-directional fluid interfacing in a microfluidic system. More specifically, the present invention relates to the use of a fluidic interface port in a microfluidic system for performing a labeling operation.

BACKGROUND OF THE INVENTION

In the chemical, biomedical, bioscience and pharmaceutical industries, it has become increasingly desirable to perform large numbers of chemical operations, such as reactions, separations and subsequent detection steps, in a highly parallel fashion. The high throughput synthesis, screening and analysis of (bio)chemical compounds, enables the economic discovery of new drugs and drug candidates, and the implementation of sophisticated medical diagnostic equipment. Of key importance for the improvement of the chemical operations required in these applications are an increased speed, enhanced reproducibility, decreased consumption of expensive samples and reagents, and the reduction of waste materials.

Microfluidic devices and systems provide improved methods of performing chemical, biochemical and biological analysis and synthesis. Microfluidic devices and systems allow for the performance of multi-step, multi-species chemical operations in chip-based micro chemical analysis systems. Chip-based microfluidic systems generally comprise conventional 'microfluidic' elements, particularly capable of handling and analyzing chemical and biological specimens. Typically, the term microfluidic in the art refers to systems or devices having a network of processing nodes, chambers and reservoirs connected by channels, in which the channels have typical cross-sectional dimensions in the range between about 1.0 µm and about 500 µm. In the art, channels having these cross-sectional dimensions are referred to as 'microchannels'.

By performing the chemical operations in a microfluidic system, potentially a number of the above-mentioned desirable improvements can be realized. Downscaling dimensions allows for diffusional processes, such as heating, cooling and passive transport of species (diffusional mass-transport), to proceed faster. One example is the thermal processing of liquids, which is typically a required step in chemical synthesis and analysis. In comparison with the heating and cooling of liquids in beakers as performed in a conventional laboratory setting, the thermal processing of liquids is accelerated in a microchannel due to reduced diffusional distances. Another example of the efficiency of microfluidic systems is the mixing of dissolved species in a liquid, a process that is also diffusion limited. Downscaling the typical dimensions of the mixing chamber thereby reduces the typical distance to be overcome by diffusional mass-transport, and consequently results in a reduction of mixing times. Like thermal processing, the mixing of dissolved chemical species, such as reagents, with a sample or precursors for a synthesis step, is an operation that is required in virtually all chemical synthesis and analysis processes. Therefore, the ability to reduce the time involved in mixing provides significant advantages to most chemical synthesis and analysis processes.

Furthermore, reduced dimensions enhance separation operations utilized in chemical synthesis and analysis processes. One example is capillary electrophoresis, which is a separation technology based on the migration of dissolved charged species through a liquid filled capillary by the application of a longitudinal electric field. By reducing the cross-sectional size of the capillaries, the separation efficiency can greatly be improved, thereby resulting in rapid separations. For examples, see Effenhauser et al., Anal. Chem. 65:2637–2642 October (1993), Effenhauser et al., Anal. Chem. 66:2949–2953 September (1994), Jacobson et al., Anal. Chem. 66:4127–4132 December (1994) and Jacobson et al., Anal. Chem. 66:1114–1118 April (1994).

Another aspect of the reduction of dimensions is the reduction of required volumes of sample, reagents, precursors and other often very expensive chemical substances. Milliliter-sized systems typically require milliliter volumes of these substances, while microliter sized microfluidic systems only require microliters volumes. The ability to perform these processes using smaller volumes results in significant cost savings, allowing the economic operation of chemical synthesis and analysis operations. As a consequence of the reduced volume requirement, the amount of chemical waste produced during the chemical operations is correspondingly reduced.

It can be concluded that due to the reduced dimensions associated with microfluidic systems, important chemical operations can be accelerated whilst at the same instance lead to a reduction of consumption of chemicals and chemical waste.

Applications of microfluidic systems are myriad. For example U.S. Pat. No. 5,922,591 describes a miniaturized integrated nucleic acid diagnostic device and system. This device is capable of performing one or more sample acquisition and preparation operations, in combination with one or more sample analysis operations. Useful applications for microfluidic systems are in nucleic acid based diagnostics and de novo sequencing applications. International Patent Appln. WO 96/04547, published Feb. 15, 1996, describes the use of electro-kinetic operated microfluidic systems for performing electrophoretic separations, flow injection analysis and chemical reactions and synthesis steps. U.S. Pat. No. 5,942,443 discloses a range of microfluidic devices and methods for performing high-throughput synthesis and analysis, especially useful in screening a large number of different chemical compounds for their effect on a variety of chemical and biochemical systems. U.S. Pat. No. 5,858,804 provides a method of performing an immunological assay in a micro-laboratory array comprising a plurality of micro-channels and chambers disposed in a solid substrate. U.S. Pat. No. 6,176,991 B1 discloses a serpentine electrophoresis channel in microchip format providing efficient, high-speed analysis of the composition of chemical samples, especially for nucleic acid sequencing.

Many methods have been described for the interfacing of fluids, e.g., samples, analytes, reagents, precursors for synthesis and buffers, towards, within or between microfluidic systems. In conventional microfluidic systems, the structures and methods used to introduce samples and other fluids into microfluidic substrates limit the capabilities of the microfluidic systems. For example, conventional microfluidic systems may include a separate sample introduction channels for introducing a sample to a microchannel for processing. The sample is first introduced into the sample channel and transported through the sample channel to the microchannel. Another method for introducing a fluid involves the use of sample wells or reservoirs in communication with the microchannel for holding a relatively larger supply of the sample. Reservoirs are structures which accommodate a significantly greater volume of fluid than the microfluidic channel. A relatively small portion of the sample supply in the sample well or reservoir is introduced into the microchannel.

The total number of samples and other fluids that can be processed on a microfluidic substrate is currently limited by the size and/or the number of reservoirs through which these fluids are introduced to the microfluidic system. A disadvantage of known structures and methods for introducing fluids into a microfluidic system is the use and transfer of a much greater volume of fluid than is needed for microfluidic analysis due to significant size inefficiencies and sample loss. Furthermore, with conventional methods of introducing fluids into microfluidic systems, it is difficult to control the amount of sample introduces that is eventually introduces into the microchannel after passing through a sample channel or a reservoir.

One method of fluidic communication with microfluidic systems is by mechanical micropumps and valves, see U.S. Pat. No. 6,033,191 and U.S. Pat. No. 5,529,465. A major disadvantage of this approach for fluidic interfacing is the complex construction and operation of these micropumps and valves. Another disadvantage is there relatively large size and internal volume when compared to the internal volume of the microchannels. Often there are multiple orders of magnitude between these two volumes and the resulting discrepancy renders micropumps unattractive to interface with a large number of small dimensional microchannels.

U.S. Pat. No. 5,173,163 describes a method and device for introducing a fluidic sample in a micro-capillary for electrophoretic separation. In this method liquid is brought into a separation capillary by introducing one end of this capillary into a vessel containing the liquid to be introduced. A combination of applied external pressures and voltages results in the transport of liquid from the vessel into the capillary. The proposed method has disadvantages. The size of the device does not allow the interfacing with a large number of microchannels, and between consecutive injections, the device needs to be cleaned, thereby considerably reducing throughput.

Another method for introducing materials in a microfluidic device is disclosed in U.S. Pat. No. 6,042,709. In this approach electrokinetic forces are employed to move a charged compound through a receiving inlet opening of the microfluidic device. A disadvantage is that the precise amount of injected liquids and substances depends upon a large number of factors which are difficult to control. One important parameter is the surface potential of the microchannel wall, which together with the applied voltage determines the liquid flow. This surface potential depends on pH of the liquid to be pumped as well as its ionic composition and even the type of ions present in the liquid. It is also a disadvantage that it does not allow the efficient interfacing with a large number of different liquids as for every injection port, a separate high voltage supply is required, together with the associated liquid channels for providing a closed electrical circuit.

A method and apparatus for performing electrophoretic experiments in a highly parallel fashion is disclosed in U.S. Pat. No. 6,103,199. Here, a plurality of separation capillaries with associated wells for receiving chemical substances in fluid form are disposed in the form of a two dimensional array. The chemical substances are dispensed from a micro titer plate into these wells by an interfacing methodology employing pressurized chambers associated with the wells to be filled. A disadvantage is that only a very small fraction of the applied liquid is actually introduced in the target microchannel, the bulk of the applied liquid drop remains behind in the well by capillary forces. As a result, most of the liquid is wasted and is not available for a consecutive chemical processing step. The effect that only a small portion of the liquid transported actually is introduced in a targeted part of a microfluidic system, can be referred to as 'injection efficiency', i.e. the ratio between the volume of liquid required for a particular chemical operation in a part of the microfluidic system, and the total volume of liquid required for the introductory operation.

In this particular disclosure, only sub-nanoliter amounts are required for the electrophoretic separation (i.e. the chemical operation), whilst many microliters of sample are drawn from the micro titer plate (i.e. introductory operation), yielding an injection efficiency much less than 0.001. A low injection efficiency is disadvantageous because it indicates inefficient use of chemical substances and an increased production of waste.

U.S. Pat. No. 6,090,251 provides micro-fabricated structures for facilitating fluid introduction into microfluidic devices. Fluid is introduced into a plurality of receiving wells in direct communication with associated microchannels, by the dropping of liquids into these receiving wells using pressurized gas. Besides the complexity of the required fluidic manifolds and pressurizing system, also here a disadvantage is the inherently low injection efficiency as only a very small fraction of the applied liquid is actually used in the experiment.

For the introduction of liquids in capillary electrophoresis columns implemented on chip-like devices, generally electrokinetic injection is applied. See Woolley et al., Anal. Chem. 70:684–688 February (1998), Jacobson et al., Anal. Chem. 68:720–723 March (1996), Jacobson et al., Anal. Chem. 66:2369–2373 July (1994) and Effenhauser et al., Anal. Chem. 67:2284–2287 July (1995). In this method, liquid is pumped from a first well towards the microchannel for electrophoretic separation by the application of a high driving voltage between this well and a second well located downstream. Due to the charged inner surfaces of the microchannel walls, an electroosmotic liquid flow is induced pumping liquid out of the first into the targeted microchannel. This method is referred to as 'electrokinetic injection' and has some specific disadvantages. One disadvantage is that if a large number of liquids need to be handled, for instance in high-throughput synthesis and screening applications, a large number of wells need to be integrated on the microfluidic device. The relatively large footprint of a typical well (about 5 mm diameter) when compared to the microchannels in which the actual chemical operation is performed (about 50 μm diameter), takes up a dominating portion of the chip surface (see U.S. Pat. No. 6,143,152 and U.S. Pat. No. 6,159,353). As the costs of microfluidic chips strongly depends on the chip surface, the required integration of wells renders this liquid injection scheme unattractive for high-throughput synthesis and screening applications.

Another disadvantage of conventional systems is that for every well, a separate electrode is required together with electronic circuitry for the application of the driving voltages. This requirement results in a complex and expensive apparatus.

Another specific disadvantage with electrokinetic injection is the fact that during the application of the driving voltage on the electrode the electrolysis of water results in the generation of hydroxyl ions ($OH^-$), hydrogen ions ($H^+$), hydrogen gas ($H_2$) and oxygen gas ($O_2$). The generated ions will affect the acidity (i.e. pH) of the liquid pumped from the first well, whilst the produced gasses potentially give rise to the formation of gas bubbles in the microfluidic system thereby destroying the experiment and eventually the microfluidic device. Besides electrolysis of the aqueous medium, any present electroactive species can degrade due to electrochemical reactions at the electrode surface. For instance, the presence of chloride ions, an ion present in most liquid media, will result in the formation of chlorine gas, which on turn can interact and potentially destroy vulnerable (biochemical) compounds present in the liquid to be injected. In addition, the liquid to be injected can contain electroactive constituents, which can be degraded by the electrochemical processes, associated with electrokinetic injection. These disadvantages can be grouped and referred to as 'electrochemical pollution'.

Another disadvantage of electrokinetic injection is that in between consecutive experiments, the well need to be thoroughly cleaned in order to prevent cross-contamination. This required cleaning step results in a reduction of throughput and makes it difficult to implement on-line monitoring. Another disadvantage is that the liquid to be injected is subjected to a high voltage. This aspect of the absence of galvanic separation makes it virtually impossible to use electrokinetic injection for in-vivo or near-vivo applications due to the danger of electrocution. Another disadvantage is that the electrokinetic injection methods referred to, are only applicable in chip like systems produced via microfabrication technology, i.e. via the use of expensive equipment and processes also applied for the fabrication of computer chips. These methods are known to have high costs. It is desirable to provide an n interfacing methodology, which is also applicable in current non chip-based capillary systems. Still another disadvantage is the low injection efficiency of electrokinetic injection. To fill a typical well, about 10–50 μl of liquid is required, whilst for a particular chemical operation only sub nanoliter amounts are required.

U.S. Pat. No. 6,130,098 discloses the movement of liquid volumes into and through microchannels by employing pressures generated by heating a volume of air in direct connection with these microchannels. A disadvantage of this fluidic interfacing method is that for a correct and efficient operation the pressure generating air chamber together with electronic heater components need to be integrated with the microfluidic system. This results in a complex device with associated large costs.

It can be concluded based on the above that current methods and systems for fluidic interfacing with microfluidic devices have particular disadvantages regarding the difficulty of integration of a large number of chemical operation nodes to interface with (i.e. electrochromatography columns, reactors etc.), relatively large required liquid volumes, low injection efficiency, electrochemical sample pollution, long rinse time between analysis steps, galvanic separation and required microfabrication technologies. Besides these disadvantages, none of the above mentioned interfacing methods allow bi-directional fluidic interfacing, i.e. transporting liquids to and from microfluidic systems. There has arisen a need in the art for providing suitable bi-directional fluidic interfacing structure that allows for the implementation of a much wider range of chemical operation steps in microfluidic systems.

SUMMARY OF THE INVENTION

The present invention provides methods, devices and systems for interfacing fluids in microfluidic systems. A fluid interface port for directly interfacing a microfluidic channel network and the surrounding environment is provided in a microchannel in a microfluidic system by forming an opening in a sidewall of the microchannel. The aperture forms a virtual wall when the microchannel is filled with a liquid. The aperture has suitable cross sectional dimensions such that capillary forces retain liquid within the microchannel. The virtual wall is defined by the meniscus of the liquid in the opening, which essentially replaces the sidewall of the microchannel so as to not substantially affect or influence fluid flow through the microchannel.

Filling of a microchannel may be accomplished via the opening in the side wall of the microchannel. To fill the microchannel, a user forms droplets of a first liquid and directs the droplet towards the opening, such that the droplets of the first liquid enter and fill the microchannel.

Fluid introduction and/or fluid removal is accomplished through a virtual wall formed in the side wall of a microchannel. The process of introducing a fluid sample to the microchannel comprises forming a droplet of the fluid and propelling the droplet towards a virtual wall. The droplet traverses the virtual wall and enters the microchannel directly, without requiring intermediate reservoirs or channels. The virtual wall formed in the sidewall of the microchannel may also define a fluid ejection port for ejecting a fluid from the microchannel in the form of a droplet.

The present invention provides a system and method for performing labeling operations on a sample. The labeling system employs a virtual wall as an interface port for one of the reactants in the labeling scheme. The system and method provide fast transient measurement of unlabeled molecules based on their binding affinity and detection of molecules based on their binding affinity.

According to one aspect of the invention, a method of labeling a sample comprises the steps of conveying the sample through a channel having a first virtual wall fluid interface port and separating the sample in the channel into a plurality of bands. The method further comprises injecting a labeling solution through the first virtual wall fluid interface port, wherein the labeling solution interacts with one of the bands to form a labeled band.

According to another aspect of the present invention, a method of labeling a sample comprises conveying the sample through a channel having a virtual wall fluid interface port and injecting a labeling solution through the virtual wall fluid interface port. The labeling solution interacts with the sample to label the sample.

According to yet another aspect of the present invention, a system for performing a labeling operation comprises a column for conveying a sample mixture through the system. The column comprises an interior bounded by a side wall. The system further includes a separation region for separating the sample mixture into a plurality of bands and a first fluid interface port downstream of the separation region for injecting labeling molecules into the interior of the column.

BRIEF DESCRIPTION OF THE DRAWINGS

FIG. 12e is a schematic view of still another embodiment of the present invention for ejecting liquid from a microchannel through a virtual wall by the application of a gas pressure pulse to the liquid.

FIG. 12f illustrates the ejector of FIG. 12e in operation.

FIG. 12g is a schematic view of an alternate means for ejecting liquid from a microchannel through a virtual wall using a pin assembly.

FIG. 21a is an exploded view of a microfluidic chip manufactured according to the teachings of the invention.

FIG. 21b is a top view of the microfluidic chip of FIG. 21a.

FIG. 21c is a side view of the microfluidic chip of FIG. 21a.

FIG. 25b shows the use of the microchannel with the virtual wall depicted in FIG. 25a.

DETAILED DESCRIPTION OF THE INVENTION

The present invention provides an improved fluidic interface for introducing fluids to and removing fluids from a microchannel in a microfluidic system. The invention further provides a method of forming the fluidic interface. The present invention significantly improves controllability over fluid samples, increases injection efficiency and reduces waste by utilizing an opening defining a virtual wall in a side wall of a microchannel to introduce and remove fluids.

One or more of the illustrative embodiments allow bi-directional fluidic interfacing to and from microfluidic systems. With the present invention, a large number of chemical operations can be performed on a small chip surface, thereby enabling the cost effective implementation and efficient operation of massively parallel synthesis and analysis systems. The present invention further significantly reduces the required liquid volume for interfacing, resulting in a considerable reduction of consumption of chemicals as well as the reduction of chemical waste. The present invention further provides methods and systems for the injection of liquids with near 100% injection efficiency and provides methods and systems for the injection of liquids which do not electrochemically pollute the handled liquids. The present invention presents methods and systems for the fast repetitive injection of liquids in microfluidic systems, pressure driven as well as electrokinetically driven, allowing high throughput synthesis, screening and analysis applications. The present invention further allows for galvanic separation of the liquid to be injected with the electrokinetically operated microfluidic system. The invention further provides fluidic interfacing with microfluidic systems devices and system that are not necessarily manufactured using standard microfabrication technologies. For example, the invention provides for interfacing with standard fused silica capillaries. The present invention applies to a variety of liquid samples, including solutions of compounds, whole cells or cell lysates, enzymes, proteins or peptides, and particles.

Figure 1:
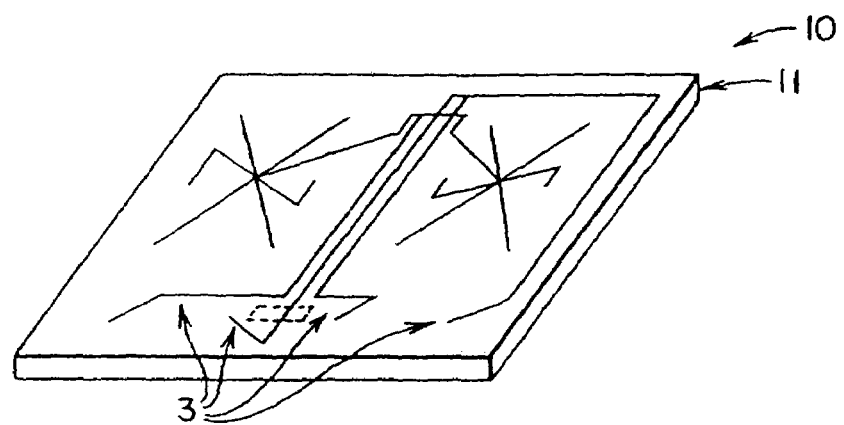
FIG. 1 is a schematic view of a microfluidic system suitable for implementing the illustrative embodiment of the invention.

FIG. 1 illustrates a microfluidic system suitable for implementing the illustrative embodiment of the present invention. The illustrative microfluidic system 10 comprises a substrate 11 having one or more microchannels 3 disposed therein. The microchannels transport fluid through the microfluidic system 10 for processing, handling, and/or performing any suitable operation on a liquid sample. As used herein, the term "microfluidic" refers to a system or device for handling, processing, ejecting and/or analyzing a fluid sample including at least one channel having microscale dimensions. The term "channel" as used herein refers to a pathway formed in or through a medium that allows for movement of fluids, such as liquids and gases. The term "microchannel" refers to a channel preferably formed in a microfluidic system or device having cross-sectional dimensions in the range between about 1.0 µm and about 250 µm, preferably between about 25 µm and about 150 µm and most preferably between about 50 µm and about 100 µm. One of ordinary skill in the art will be able to determine an appropriate volume and length of the microchannel. The ranges are intended to include the above-recited values as upper or lower limits. The microchannel can have any selected shape or arrangement, examples of which include a linear or non-linear configuration and a U-shaped configuration. The microfluidic system 10 may comprise any suitable number of microchannels 3 for transporting fluids through the microfluidic system 10.

According to one practice, the microchannel of the present invention can include a fluid interface port. As used herein, "fluid interface port" refers to a structure in a microfluidic system, such as an aperture formed in a microchannel, which provides fluid access between the interior and the exterior of a microchannel. The fluid interface port is utilized to introduce fluids and other material to the microchannel and/or to remove fluid and/or other material from the microchannel. The fluid interface port may comprise, among other applications, a filling port for filling the microchannel with a carrier liquid, a sample introduction port for introducing a sample into the microchannel and an ejection port for ejecting fluid from the microchannel.

According to the illustrative embodiment, the microchannel is defined by a side wall having any suitable shape enclosing at least a portion of the interior of the channel. The fluid interface port is formed in the side wall of the microchannel by removing a portion of the side wall to define an opening. The fluid interface port of the illustrative embodiment is formed by an aperture in the side wall of the microchannel having a diameter of between about 0.1 µm and about 200 µm and preferably between about 25 µm and about 125 µm and most preferably between about 50 µm and about 100 µm. The aperture forming the fluid interface port may have any suitable shape, including, but not limited to, a cylinder, a disk, a conical shape, an elliptical shape and a cubic shape. The side wall or wall of the microchannel can be formed by two or more components that bound the entire volume of the microchannel. According to a first aspect of the invention, the fluid interface port is utilized to fill the microchannel with a first liquid. The first liquid comprises a carrier fluid for transporting a sample, reagent or other suitable liquid for performing one or more chemical operations, such as reactions and separations. Fluid flow may be induced in the microchannel via any suitable means, including, but not limited to, pressurizing and electroosmotic means.

As illustrated in FIG. 2a through FIG. 7, the fluid interface port 17 formed in the sidewall of the microchannel forms a filling aperture or microaperture for filling the microchannel with the first liquid. Typically, conventional microchannels are filled by inserting the end of the microchannel into a reservoir containing the first liquid. Capillary forces pull the first liquid into the microchannel and thereby fill the microchannel with the first liquid. In order to avoid this procedure, the present invention employs a fluid interface port formed in the sidewall (not end) of the microchannel. This enables a user to fill the microchannel through the port to provide simple, fast and efficient filling without requiring a large, separate liquid reservoir.

Figure 2A:
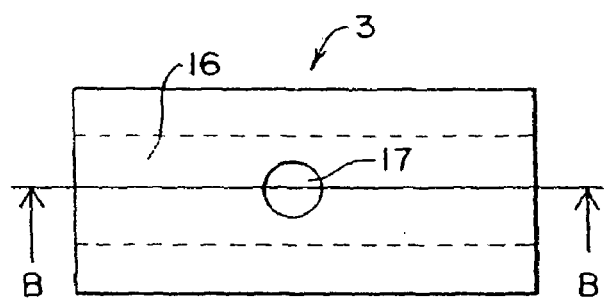
FIG. 2a is a top view of a microchannel structure having a fluid interface port formed in a side wall of the microchannel for filling the microchannel with a first fluid according to the teachings of the invention.
Figure 2B:
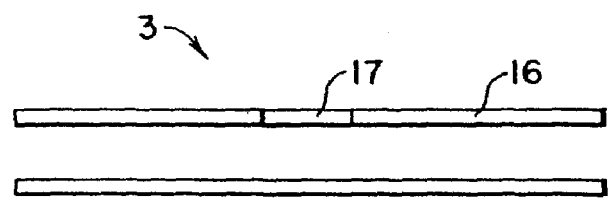
FIG. 2b is a cross-sectional view of the microchannel of FIG. 2a along the length of the microchannel.

FIG. 2a is a top view of a microchannel structure 3 comprising a side wall 16 surrounding a hollow interior. The microchannel includes a fluid interface port 17 located in the side wall 16 of the microchannel structure. The fluid interface port 17 may have any suitable shape based upon the intended use, examples of which include circular, cylindrical, elliptical and conical. FIG. 2b is a cross-sectional view of the microchannel structure taken along the length of the microchannel 3, showing the fluid interface port 17 disposed in the top side of the microchannel. As shown, the interior of the microchannel 3 is initially empty. According to the illustrative embodiment, the microchannel 3 is filled with a first liquid via the fluid interface port 17 formed in the side wall 16 of the microchannel.

Figure 3A:
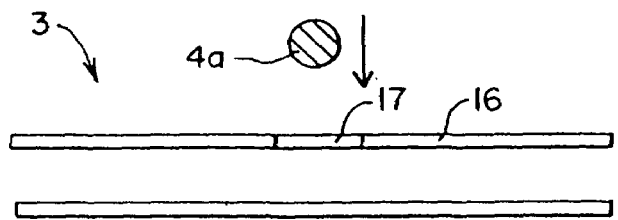
FIGS. 3a and 3b illustrate the steps of filling the microchannel of FIG. 2a with a first fluid by directing droplets of the first fluid through the fluid interface port.
Figure 3B:
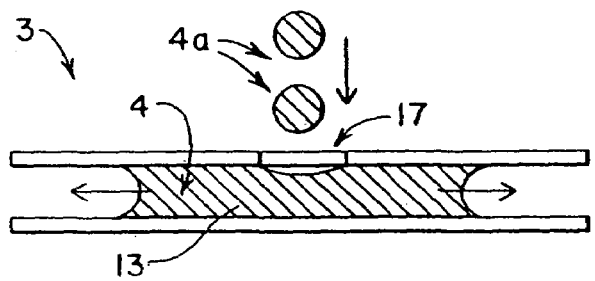

FIGS. 3a and 3b illustrate the process of filling the microchannel structure 3 with a first liquid 4 by directing droplets 4a of the first liquid 4 toward the fluid interface port 17. The droplets 4a enter the microchannel 3 through the fluid interface port 17 and form a plug 13 of the first liquid 4 within the microchannel 3. As more droplets 4a are introduced via the fluid interface port 17, the plug 13 expands in both directions through the microchannel, as indicated by the arrows, thereby filling the microchannel along the length of the microchannel with the first liquid 4. Moreover, capillary forces work to draw the liquid 4 along the length of the microchannel 3. According to the illustrative embodiment, the first liquid 4 forms a meniscus in the fluid interface port 17 when the microchannel is filled and the liquid is retained in the microchannel by capillary forces.

The fluid interface port 17 is sized and dimensioned to form a virtual wall 15 when the microchannel is filled with the first liquid 4. As used herein, "virtual wall" refers to the meniscus formed by the first liquid 4 in the port 17 formed in the side wall of the microchannel. The meniscus surface can be, although not required, substantially co-planar with the wall 16 of the microchannel in which the meniscus is formed. The meniscus essentially replaces the removed portion of the side wall that defines the aperture 17. The word "virtual" is chosen to express the effect that the overall liquid flow through the microchannel of the microfluidic system is not influenced by the virtual wall, i.e. the flow of liquid in the microfluidic system having a virtual wall is substantially identical to the flow of liquid through an identical microfluidic system in which no virtual wall is present. The fluid interface port, according to one practice, has appropriate dimensions and surface properties as to substantially not influence the overall liquid flow and liquid shape when compared to a microfluidic system in which no port or meniscus is formed. The virtual wall forms a direct interface between the microchannel interior 5 and the microchannel exterior, allowing direct access to the liquid in microchannel 3 without introducing dead or unswept volume in the microchannel 3. The virtual wall also serves to seal liquid inside of the microchannel through a range of pressures in the microchannel. Those of ordinary skill will readily recognize that the surface or wall of the fluid interface port can be formed anywhere along the axial height of the port. One of ordinary skill will recognize that the meniscus may be convex or concave, depending on the appropriate system pressure.

Figure 4A:
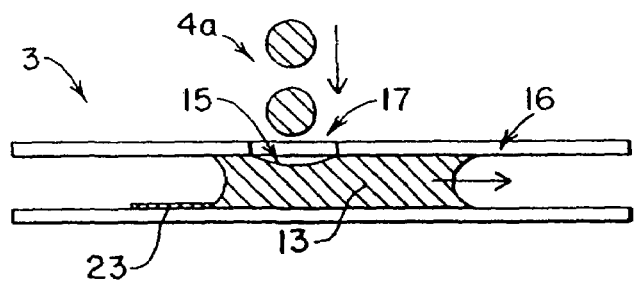
FIG. 4a illustrates the microchannel of FIGS. 2a and 2b further including a hydrophobic patch disposed in the microchannel interior according to an alternate embodiment of the present invention.

According to an alternate embodiment, shown in FIG. 4a, a hydrophobic patch 23 is applied to the side wall or interior of the microchannel 3 prior to introduction of the first liquid 4. When the first liquid 4 is introduced to the microchannel, the hydrophobic patch 23 forms a barrier, and causes the plug 13 of liquid 4 to expand only in one direction, away from the patch 23.

Figure 4B:
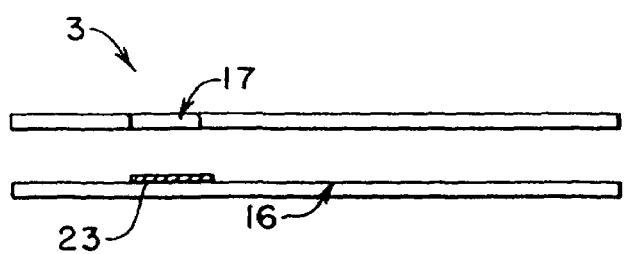
FIG. 4b illustrates an alternate embodiment of a microchannel according to the teachings of the invention, wherein the hydrophobic patch is coaxially arranged with a fluid interface port.

According to one embodiment, shown in FIG. 4b, the hydrophobic patch 23 is applied to the interior surface of the microchannel through an aperture forming a fluid interface port 17 in the sidewall 16 of the microchannel. The hydrophobic patch 23 may comprise any suitable material for rendering a surface hydrophobic, such as gold. The hydrophobic material may be sputtered, evaporated, sprayed or deposited through the aperture 17 and bound to the interior surface of the microchannel 3 opposite the aperture to form the hydrophobic patch 23. One skilled in the art will recognize that any suitable surface treatment for the microchannel may be applied through the aperture, in addition to hydrophobic patches.

The aperture used to apply the hydrophobic patch 23 may further serve as a vent for the microchannel 3 to allow air to escape from the microchannel interior. As shown, the aperture is coaxially arranged with the hydrophobic patch. The actual vent, formed by the aperture 17 in the side wall, is not hydrophobic. However, the microchannel surface coaxially opposite the vent is rendered hydrophobic by application of the hydrophobic patch 23. The hydrophobic region is not flushed by liquid, allowing air to escape the microchannel interior through the aperture 17 in the side wall 16.

Figure 5A:
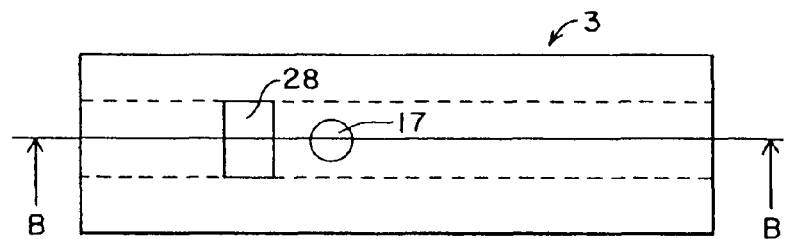
FIG. 5a is a top view of a microchannel according to one embodiment, including a filling aperture and a stopper hole for directing the filling of a first fluid in the microchannel according to the teachings of the invention.
Figure 5B:
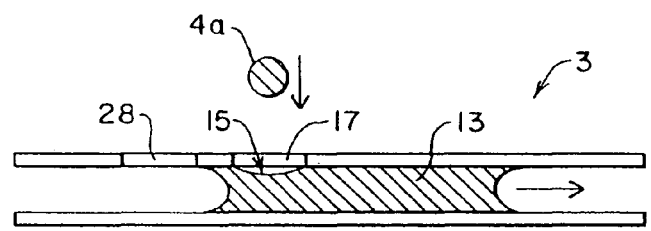
FIG. 5b is a cross-sectional view of the length of the microchannel shown in FIG. 5a, illustrating the process of filling the microchannel.

According to yet another embodiment, shown in FIGS. 5a and 5b, the microchannel 3 further includes a stopper hole 28 adjacent to the fluid interface port 17. The stopper hole 28 is sized and dimensioned to form a pressure barrier for a liquid disposed in the microchannel. One of ordinary skill in the art will be able to determine a suitable size and dimension of the stopper hole to create the pressure barrier. The stopper hole 28 acts as a stop for the meniscus of liquid filling the microchannel, such that the liquid plug 13 formed by the first liquid 4 extends only in one direction along the length of the microchannel 3, away from the stopper hole 28.

According to yet another embodiment, the cross-sectional dimensions of the microchannel 3 may be varied locally to affect the pressure within the microchannel interior. For example, the microchannel may be narrowed or widened at certain locations to increase or decrease the capillary forces acting on a fluid in the microchannel interior. One of ordinary skill in the art will be able to determine a suitable cross-sectional dimension to achieve a desired pressure within the microchannel interior.

Figure 6:
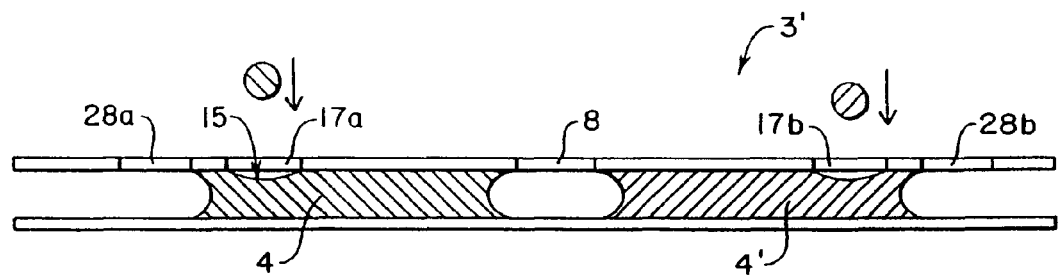
FIG. 6 illustrates the filling of a microchannel with two different fluids by utilizing a plurality of filling apertures disposed in the side wall of the microchannel.

Alternatively, as shown in FIG. 6, the microchannel 3' includes two fluid interface ports 17*a* and 17*b*, two stopper holes, 28*a* and 28*b*, and a vent hole 8 disposed between the two fluid interface ports 17*a* and 17*b* to allow for filling of the microchannel 3' with a plurality of different liquids. A first liquid 4 is introduced into the interior of the microchannel through the first fluid interface port 17*a*. The first stopper hole 28*a* causes the first liquid to extend along the microchannel towards the vent hole 8. A second liquid 4' is introduced into the interior of the microchannel through the second fluid interface port 17*b* and extends along the microchannel towards the vent hole 8, due to the presence and location of the second stopper hole 28*b*. Air in the microchannel is released through the vent hole 8.

Figure 7A:
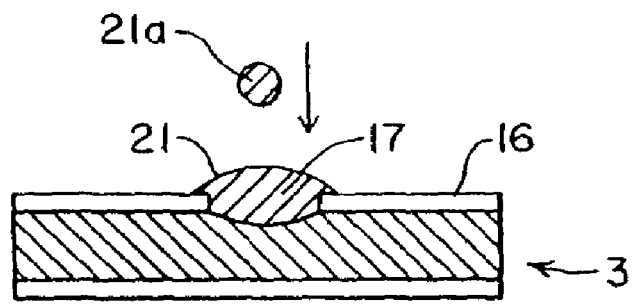
FIG. 7a illustrates the process of closing the filling aperture of FIGS. 2a through 6 by forming and dispensing drops of encapsulant onto the filling aperture according to one embodiment of the present invention.
Figure 7B:
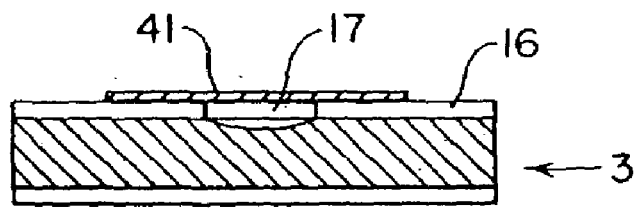
FIG. 7b illustrates the process of closing the filling aperture using a covering layer according to an alternate embodiment of the present invention.

After filling the microchannel via a fluid interface port 17, such as a filling hole disposed in the sidewall of the microchannel, the fluid interface port may be closed to prevent leakage of the fluid from the microchannel. According to the embodiment shown in FIG. 7*a*, the fluid interface port 17 is closed by dispensing drops of encapsulant 21*a* onto the fluid interface port 17. The encapsulant drops form a cap 21 and effectively close the microchannel 3. Alternatively, as shown in FIG. 7*b*, the microchannel 3 may be closed after filling by adhering a closing layer 41 to the microchannel 3 to cover the fluid interface port 17.

Figure 8:
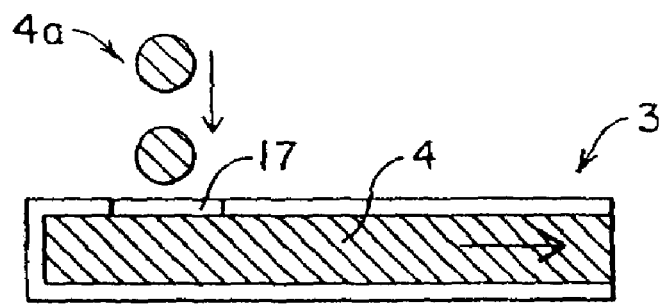
FIG. 8 illustrates a microchannel having a filling aperture located adjacent to a closed end of the microchannel, such that the introduction of droplets into the microchannel through the filling aperture induces a flow in the microchannel.

According to another embodiment, as shown in FIG. 8, the fluid interface port 17 may be utilized to provide a pumping mechanism to induce movement of liquid through the microchannel. As illustrated, the fluid interface port 17 may be disposed adjacent to a closed or open end of the microchannel 3. The introduction of droplets into the microchannel through the fluid interface port results in movement of liquid through the microchannel. This movement corresponds to the frequency of the drops introduced to the hole. The movement of liquid induced by the introduction of droplets through the filling hole can be applied in many microfluidic applications as an accurate pumping and/or dosing mechanism. Those of ordinary skill will readily recognize that the microchannel can employ a hydrophobic patch or a stopper hole to induce liquid movement in a selected direction or any suitable means for conveying liquid through the microchannel.

Figure 9A:
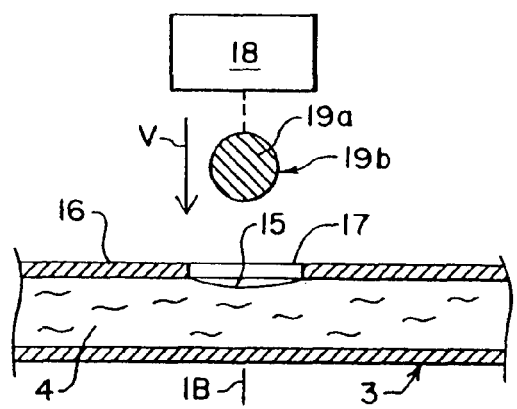
FIG. 9a is a cross-sectional side view of a microchannel including a fluid interface port for receiving a liquid droplet into the microchannel.

According to another aspect of the invention, a second fluid sample can be introduced to the microchannel 3 through the same or different fluid interface port 17, after the microchannel is filled with the first liquid 4. FIG. 9*a* is a side view of a microchannel 3 according to an illustrative embodiment of the invention including a fluid interface port 17 formed in the side wall 16 of the channel and showing a droplet generating system 18 for forming droplets of the second fluid sample to be introduced into the microchannel 3. The fluid interface port 17 provides a direct interface between the microchannel interior and the exterior. According to the present invention, the interface between a first liquid 4 in the microfluidic system and a surrounding gas phase is defined by the local absence of a solid wall in the microchannel, rather than a separate channel or reservoir structure.

According to one aspect, the virtual wall 15 formed in the port 17 can be used as a sample introduction port for introducing the second liquid into the first liquid 4 in the form of liquid droplets. A second liquid 19*a* can be directly injected into the first liquid 4 within microchannel 3 through the virtual wall 15 without requiring an intermediate structure, such as a sample introduction channel or a sample reservoir. According to the illustrative embodiment, the second liquid is introduced by forming a droplet 19*b* of the second liquid 19*a* and directing the droplet towards the virtual wall 15 with an appropriate speed and direction, indicated in FIG. 9*a* by velocity vector V, so as to traverse the virtual wall 15 and enter the interior of the microchannel.

The liquid droplets may be formed and dispensed using any suitable droplet forming system 18, such as the droplet dispensing systems described in U.S. Provisional Patent Application Ser. No. 60/325,001 filed Sep. 25, 2001 and entitled "Two-Pin Liquid Sample Dispensing System", the contents of which are herein incorporated by reference, and U.S. Provisional Patent Application No. 60/325,040 entitled "Droplet Dispensing System", the contents of which are herein incorporated by reference.

According to the illustrative embodiment, the lateral dimensions of the fluid interface port 17 are substantially identical to or less than the diameter of the microchannel 3, whilst the diameter of the illustrated droplet 19*b* is smaller than the lateral dimensions of the fluid interface port 17. The fluid interface port 17 has a dead volume that is substantially smaller when compared to conventional fluid interface ports, such as a well or a sample introduction channel. As used herein, "dead volume" refers to the volume of liquid retained in the fluid interface port 17 (i.e. the volume of liquid the fluid interface port holds that is not flushed through the fluid interface port by the flow field of the first liquid 4 through the microchannel). The total volume of the fluid interface port 17 is defined by the area of the aperture formed in the side wall and the thickness of the sidewall 16. The volume of the first liquid 4 filling the fluid interface port defines the dead volume. According to the illustrative embodiment, the fluid interface port has a dead volume that is less than about one nanoliter and preferably less than one picoliter, and most preferably about zero. Preferably, the dead volume is less than the volume of liquid sample that is injected through the fluid interface port 17.

The size of the aperture and the hydrophobicity of the fluid interface port determine the size of the dead volume. For example, the microchannel shown in FIG. 9*a* has zero dead volume i.e. no liquid is retained in the fluid interface port 17 and a sample injected through the port 17 directly enters the microchannel interior. According to other embodiments, the first liquid may partially or totally fill the aperture, and the dead volume may be a non-zero, but substantially small, value. The dead volume also depends in whether the meniscus 15 bulges up or down, a factor that is controlled by the hydrophobicity of the port 17, the properties of the liquid filling the microchannel 3 and the size of the aperture forming the port 17.

The relatively small dead volume provided by the virtual wall 15 results in a direct fluid interface allowing direct injection of a precise volume of sample into the interior of the microchannel 3 from the exterior of the microchannel. The ability to directly inject sample into the microchannel due to the low dead volume of the fluid interface port 17 provides improved control over the amount of sample that is injected into the microchannel, allows efficient use of sample, and significantly reduces waste of the sample. Furthermore, the direct injection provided by the very small dead volume reduces or prevents cross-contamination between different samples and allows a third liquid to be directly injected into the system immediately after a second liquid without requiring flushing of the fluid interface port. Conversely, in conventional microfluidic systems employing a sample introduction channel, sample well or sample reservoir for introducing a fluid sample to a microchannel, the dead volume is significantly large relative to the size of the microchannel. In order to introduce a fluid sample into the microchannel interior, the fluid sample must first pass through the dead volume. A larger dead volume leads to dispersion of the sample, a time delay between the time of injection and the time when the sample enters the microchannel, injection inefficiency, potential cross-contamination between different samples and difficulty controlling the amount of sample that actually reaches the microchannel. These problems are avoided or reduced by the use of the fluid interface port 17 forming a virtual wall 15 according to the illustrative embodiment.

Figure 9B:
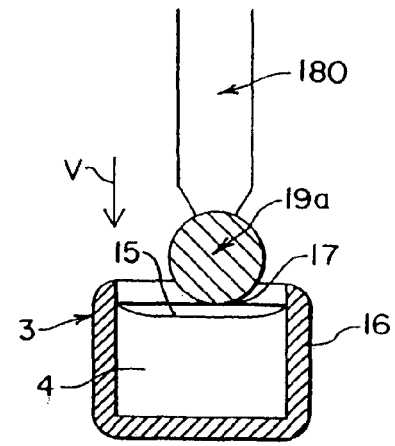
FIG. 9b is a cross-sectional view perpendicular through the microchannel of FIG. 9a at the position of the fluid interface port, illustrating the insertion of a drop using a pin.

FIG. 9b shows a cross-sectional view perpendicular to the microchannel 3 at the location of fluid interface port 17, illustrating the process of introducing the second liquid 19a into the first liquid 4 through the virtual wall 15. As illustrated in FIG. 9b, the droplet generating system 18 comprises a droplet carrying element for carrying the droplet. According to the illustrative embodiment, the droplet carrying element 180 comprises a pin, as described in U.S. Provisional Patent Application Ser. No. 60/325,001 filed Sep. 25, 2001 and entitled "Two-Pin Liquid Sample Dispensing System", and U.S. Provisional Patent Application No. 60/325,040 entitled "Droplet Dispensing System", for introducing the droplet to the aperture by contacting the virtual wall 15.

Figure 9C:
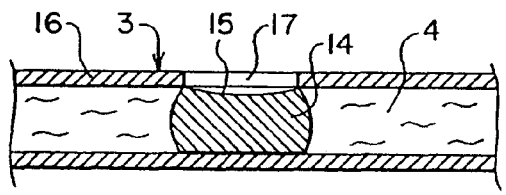
FIG. 9c is a cross-sectional view of a microchannel having a virtual wall according to the teachings of the invention, illustrating the composition of the liquid inside the microchannel directly after receiving a droplet.

FIG. 9c shows a cross-sectional view of the microchannel 3 immediately after injection of the second liquid 19a in the first liquid 4. As illustrated, the second liquid 19a forms a well defined plug 14 in the first liquid 4. According to an alternate embodiment, the second liquid dissolves, merges or mixes into the first liquid. After introduction via the virtual wall, the second liquid 19a is transported through the microchannel by the first liquid 4.

Figure 9D:
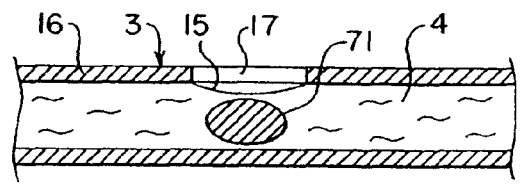
FIG. 9d illustrates a microchannel having a virtual wall according to the teachings of the invention, immediately after injection of the second liquid in the first liquid, whereby the first and second liquid are immiscible.

According to one embodiment of the invention, illustrated in FIG. 9d, the second liquid, which is introduced into the microchannel 3 via the virtual wall, is immiscible with the first liquid. FIG. 9d shows a cross-sectional view of the microchannel 3 immediately after injection of the immiscible second liquid 19a in the first liquid 4. After penetrating the virtual wall 15, a substantially spherical, micelle-like liquid volume 71 of the second liquid is formed in the first liquid 4. As both liquids are immiscible with each other, this liquid volume 71 remains confined and can be separately transported along the microchannel 3.

The illustrative mode of liquid injection into a microfluidic system via a virtual wall and consecutive handling is particularly preferable for performing a liquid-liquid extraction. Liquid-liquid extraction is a well-known technique, widely used in many chemical analysis and synthesis steps, especially during drug discovery. In liquid-liquid extraction, two immiscible liquids are brought in intimate contact to allow the extraction of specific components from the liquid containing a specific substance (i.e. the source liquid) into the extraction medium (i.e. the target liquid). A suitable example of liquid-liquid extraction is the extraction of a water-soluble substance synthesized in an organic solvent, whereby said solvent is immiscible with water. The organic solvent containing the water-soluble synthesis product of interest is mixed with water to form small micelle-like droplets of solvent in the water phase. The water soluble substance diffuses out of the solvent and is collected in the water phase. The water phase can be re-collected after a predetermined time, due to the immiscible properties of the two substances. In this manner, the water soluble substance is thus extracted from the organic liquid phase. Of key importance is the total contact surface between both liquids. A larger exchanging surface, provided by the shape of the droplets, results in a faster extraction process.

The microfluidic system of the present invention may be utilized to perform a liquid-liquid extraction between a water soluble substance and an organic liquid phase, which is immiscible with water, as described below. To perform a liquid-liquid extraction between a water soluble substance and an organic liquid phase, the illustrative microchannel 3 is filled with a suitable first liquid 4, which is, according to the illustrative embodiment, an appropriate aqueous solution. The first liquid 4 forms a virtual wall 15 at the opening 17 disposed in the sidewall of the microchannel. Droplets 19b of the organic phase containing the substance are formed and injected into the first liquid 4 through the virtual wall 15. After the droplets 19b traverse the virtual wall, micelle-like liquid volumes 71 are formed in the microchannel 3, which, due to their very small size, have a relatively very large exchange surface area. Consequently, the water soluble substance initially present in the micelle-like liquid volumes 71 is extracted into the first liquid 4 and is available for further processing. To concentrate the substance in a consecutive step, the extracted micelle-like liquid volumes 71 are separated from liquid 3 by a suitable separating technique as known in the art, including, but not limited to, electrophoresis, dielectrophoresis, gravitational or body forces, capillary forces and special selective sieves.

Figure 9E:
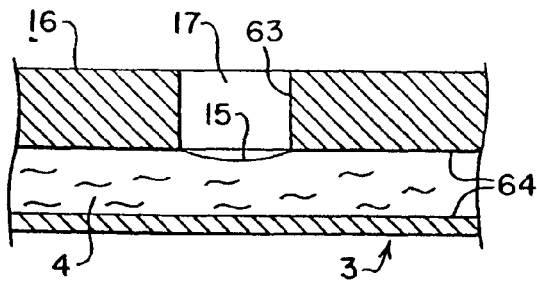
FIG. 9e is a cross-sectional view of a microchannel having a virtual wall according to an alternate embodiment of the invention.

According to an alternate embodiment, shown in FIG. 9e, the fluid interface port 17 disposed in the microchannel side wall 16 and forming a virtual wall 15 may have any suitable shape, such as a cylindrical or conical shape, having a suitably low dead volume for providing direct access to the microchannel interior. According to one embodiment, the inner wall 63 of the fluid interface port 17 is formed of or coated with a material that is repellant for the first liquid 4 to repel the first liquid from the opening 17. According to a preferred embodiment, the inner wall 64 of the microchannel 3 is attractive for the first liquid 4, to retain the first liquid inside the microchannel. The liquid repellent section in the fluid interface port 17 prevents liquid from leaking out of the microfluidic system and ensures the repeatable formation of a virtual wall 15 in the fluid interface port 17 when the microchannel is filled with liquid. The use of an inner wall 64 that is attractive for the first liquid 4 further enhances automatic, passive capillary filling of the microchannel 3 via the port 17, as described above, or by providing the first liquid 4 at one end of the microchannel 3. As a result of capillary forces, the microchannel 3 may be automatically filled without requiring application of external energy or pressure sources, such as pumps or pressure chambers.

Figure 9G:
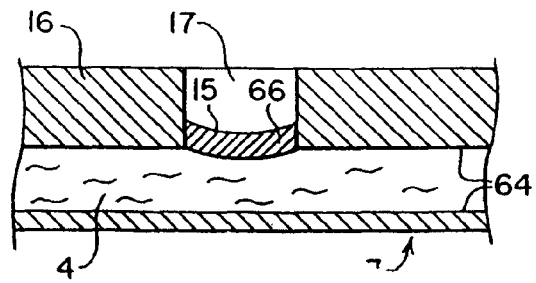
FIG. 9g is a cross-sectional view of a microchannel having a virtual wall according to an alternate embodiment of the invention, including a covering layer.
Figure 9F:
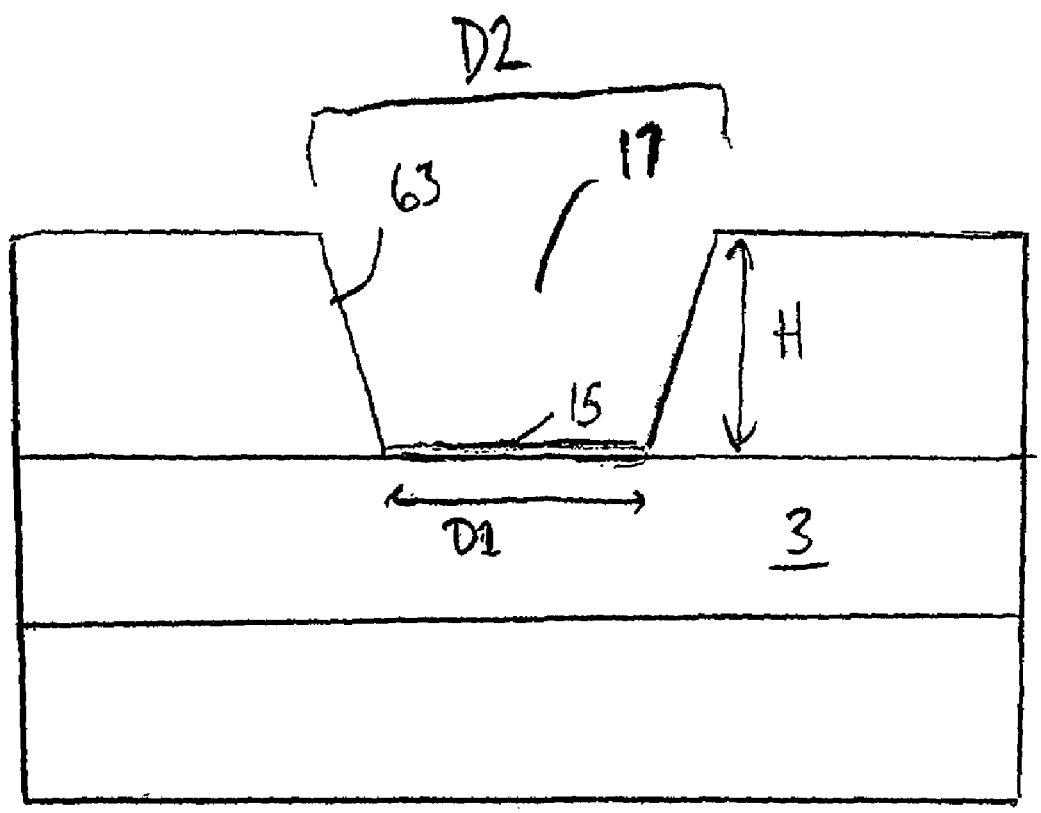
FIG. 9f illustrates a microchannel having a conical fluid interface port forming a virtual wall according to another embodiment of the invention.

As shown in FIG. 9f, the fluid interface port 17 may have an inverted conical shape to facilitate formation of the virtual wall when the corresponding microchannel 3 is filled with liquid. For example, the shaft forming the fluid interface port 17 may have a height H of about 0.175 mm, with an aperture at the bottom having a diameter D1 of between about 0.05 mm and about 0.2 mm, preferably about 0.1 mm, and an aperture in the top of the fluid interface port 17 having a diameter D2 of between about 0.2 and 0.3 mm, and preferably about 0.25 mm. As shown, the meniscus, defining the virtual wall 15, is formed at the bottom of the shaft and has a diameter of about 0.1 mm upon filling of the microchannel 3.

FIG. 9g illustrates an embodiment where the microchannels and virtual wall 15 are covered with a covering layer 66. According to the illustrative embodiment, the covering layer 66 comprises a liquid layer that is immiscible with the first liquid 4 in the microchannel. The covering layer prevents the evaporation of the first liquid 4 from the microchannel through the opening 17, while still allowing the injection of a second liquid, such as liquid 19a, into the microchannel through the covering layer 66 and the virtual wall 15.

Figure 9H:
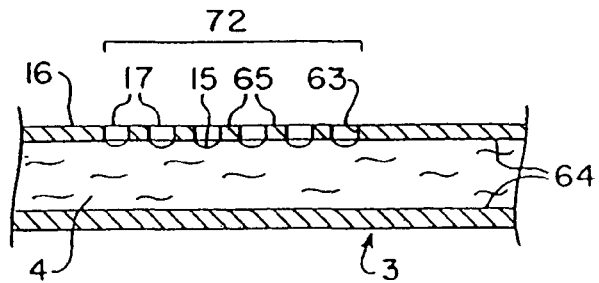
FIG. 9h is a cross-sectional view of a microchannel having an array of apertures forming virtual walls.
Figure 9I:
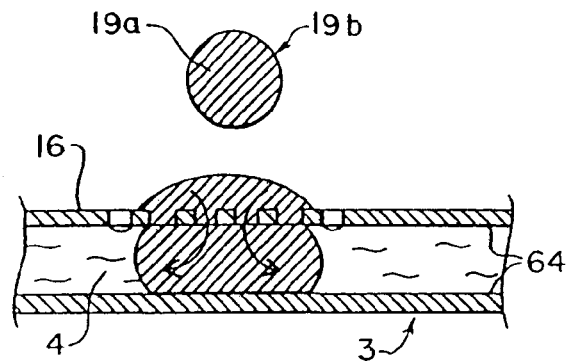
FIG. 9i illustrates the introduction of a liquid into the microchannel shown in FIG. 9h.

According to an alternate embodiment, as shown in FIG. 9h, the fluid interface port in the microchannel is formed by an array 72 of openings 17, each forming a virtual wall 15 upon filling of the microchannel 3 with the first liquid 4. The virtual walls 15 in the array 72 are disposed in close proximity to each other, thereby allowing the injection of liquid via a wicking process, as illustrated in FIG. 9i. To introduce a second liquid into the microchannel, as shown in FIG. 9i, a selected amount of the second liquid 19a is deposited on top of the array 72, such that the capillary forces wick the second liquid into the microchannel 3. According to a preferred embodiment, the inner walls 63 of the fluid interface port 17 are rendered repellant to the first liquid 4 whilst the outer surfaces 65 of the fluid interface ports 17 preferably are rendered attractive to the second liquid 19a. The use of an array of openings to form an array of virtual walls reduces the necessity and criticality of precisely targeting the droplets 19b towards a particular virtual wall. The droplets need only to be aimed in the direction of the array, allowing capillary forces to pull droplets into the channel interior. The velocity and direction of the propelled droplets are also not as important to achieve injection of the sample into the microchannel 3.

Figure 10A:
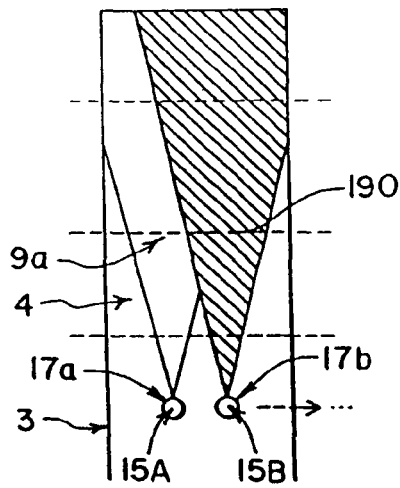
FIG. 10a illustrates a microchannel having a plurality of virtual walls disposed across the radial width of the microchannel according to one embodiment of the present invention.

According to yet another embodiment of the invention, a plurality of openings are disposed in the sidewall of the microchannel to allow for the introduction or ejection of liquid via a virtual wall at a plurality of locations in the microchannel. For example, as shown in FIG. 10a, the microchannel can include multiple fluid interface ports 17a, 17b positioned across or along the width of the microchannel 3 to define a plurality of virtual walls to allow for simultaneous introduction of a plurality of liquids. In this manner, an increased volume of liquid may be immediately injected into the microchannel 3 via the plurality of virtual walls. The use of a plurality of virtual walls across the microchannel width further allows for simultaneous introduction and mixing of a plurality of different liquids. As shown in FIG. 10a, the microchannel includes a first liquid 4. A second liquid 19a may be introduced via a first virtual wall 15a. Simultaneously, a third liquid 190a may be introduced via a second virtual wall 15b. The second liquid 19a and the third liquid 190a mix together with the first liquid 4, as illustrated by the diffusion profiles of the liquids.

Figure 10B:
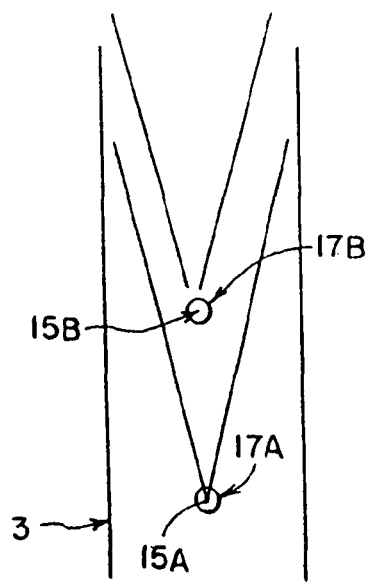
FIG. 10b illustrates a microchannel having a plurality of virtual walls disposed along the axial length of the microchannel according to one embodiment of the present invention.

Alternatively, as shown in FIG. 10b, the microchannel 3 may include a plurality of virtual walls disposed along the length of the microchannel to allow for sequential introduction of liquids into the microchannel, or ejection of a liquid from the microchannel along different locations in the fluid flow path.

Figure 11A:
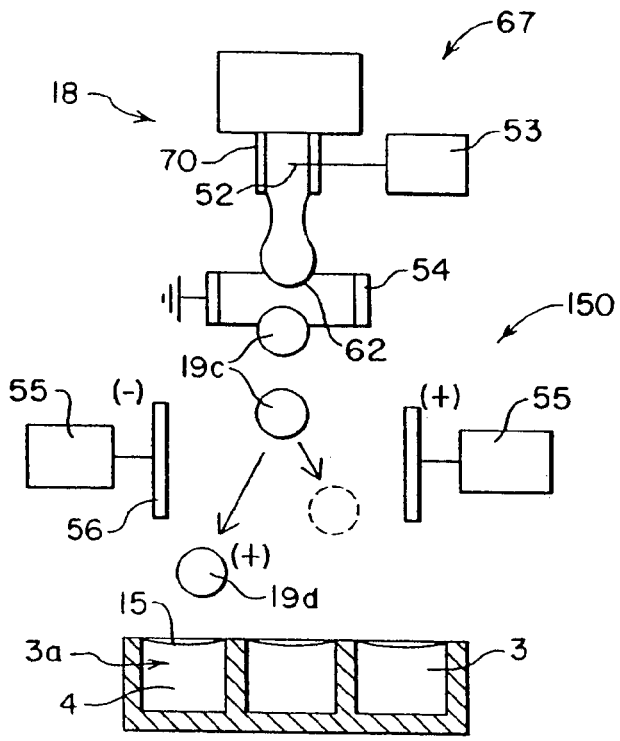
FIG. 11a is a schematic block diagram representative of a sample introduction system for electrically guiding a selected droplet into a selected microchannel according to the teachings of the present invention.

The illustrative microfluidic system 10 employing a virtual wall 15 in a fluid interface port may be utilized with a sample introduction system for forming and guiding a droplet into a microchannel via a virtual wall. FIG. 11a illustrates the microfluidic system 10 employing a suitable sample introduction system 67 for guiding a charged droplet 19d of a selected sample into a microchannel 3a of selected interest. The illustrated sample introduction system 67 includes a droplet generator 18 for forming droplets of a selected liquid, a droplet charging circuit 53 for selectively charging a droplet, and a droplet guiding system 150, comprising a ground electrode 54 and a plurality of electrically controlled deflection plates 56, 57, for establishing an electrostatic field to direct the charged droplets to a selected location. The illustrative microfluidic system 10 can be coupled to electronics for controlling the formation and guidance of the droplet to a selected microchannel.

The droplets are generated by the droplet generator 18 having a nozzle assembly 70. The nozzle assembly 70 ejects liquid and forms individual droplets of the liquid at a breaking off point 62. The droplet charging circuit 53 is pre-programmed and a corresponding electrode 52 is positioned within the nozzle assembly to charge a pre-selected droplet with either a positive or negative charge at the breaking off point 62. Surrounding the breaking off point 62 of the droplet formation is a ground electrode 54. After breaking off and passing the ground electrode 54, the charged droplet 19c travels through an electrostatic field established by the first electrically controlled deflection plate 56 and the second electrically controlled deflection plate 57. A plate-charging circuit 55 is associated with each plate and controls the polarities thereof to provide proper electrical charging to the respective deflection plates. As shown in FIG. 11a, the droplet 19d is charged positively and is deflected towards a virtual wall 15 disposed in the selected microchannel 3a by negatively charging the first plate 56 and positively charging the second plate 57. By controlling the charge on individual droplets with droplet charging circuit 53 as well as controlling the electric field between the first plate 56 and the second plate 57, droplets can be guided and effectively targeted to a particular channel to effect pre-programmed chemical experiments.

Figure 11B:
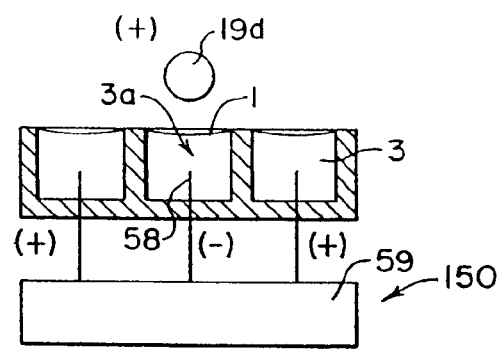
FIG. 11b is a cross-sectional view of a microchannel array of FIG. 4a of the present invention wherein microchannels can selectively be charged to attract or repel a selected droplet according to the teachings of the present invention.

FIG. 11b is a cross-sectional view of a plurality of microchannels 3 with associated fluid interface ports 17 employing a different charging technique according to an alternate embodiment of the present invention. In the embodiment shown in FIG. 11b, the droplet guiding system 150 comprises an electrode 58 for each microchannel in the system and a channel charging circuit 59 for charging the microchannels. Each microchannel 3 includes a corresponding electrode 58 for enhanced targeting of the droplets by selectively charging the corresponding microchannel. The electrode 58 is connected to the channel charging circuit 59, associated with the droplet charging circuit 53 shown in FIG. 11a, for generating a selected charge in each of the microchannels 3. The channel charge interacts with the charged droplets to guide or steer the charged droplet 19d towards a respective microchannel 3a. As seen in FIG. 11b, the droplet 19d is positively charged whilst a selected microchannel 3a is charged negatively, thereby resulting in an attractive force between the positively charged droplet 19d and the virtual wall 15 of the negatively charged microchannel 3a. Guiding is enhanced by charging neighboring microchannels 3b and 3c with identical sign as the selected droplet 19d, which consequently repel the positively charged droplet 19d towards the selected microchannel 3a.

Figure 11C:
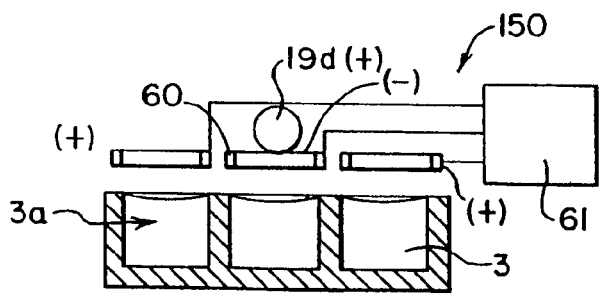
FIG. 11c is a cross-sectional view of the microchannel array of FIG. 11a employing an array of ring electrodes for guiding a selected droplet into a selected microchannel according to the teachings of the present invention.

FIG. 11c shows an alternate approach to enhance targeting of a charged droplet 19d into a selected microchannel 3a of a plurality of microchannels 3, according to the present invention. In the embodiment shown in FIG. 11c, the droplet guiding system 150 comprises a plurality of targeting electrodes 61, each associated with a corresponding fluid interface port or microchannel. The fluid interface ports and corresponding microchannels are charged by a targeting electrode charging circuit 61 to result in a force towards the virtual wall 15 of the selected microchannel 3a. As seen in FIG. 11c, the selected droplet 19d is positively charged whilst the targeting electrode 61 associated with the selected corresponding microchannel 3a is charged negatively to guide the selected droplet 19d into a selected corresponding microchannel 3a via the virtual wall 15. Guiding is enhanced by charging a neighboring targeting electrode 61 with an identical sign as the selected droplet 19d to repel the droplet away from the neighboring microchannels 3b, 3c and towards the selected microchannel 3a.

According to an alternate embodiment of the invention, the droplet guiding system 150 may comprise a machine vision system that can employ fiducial marks on one or more components of the system. One skilled in the art will recognize that any suitable droplet guiding system for directing a droplet towards a virtual wall may be utilized in accordance with the teachings of the invention.

According to the present invention, the fluid interface port 17 of the microfluidic system 10 can optionally be utilized as a bi-directional fluidic interface for the microchannel. In addition to providing an interface for introducing a sample to a microchannel, the illustrative virtual wall formed in the microchannel 3 filled with the first liquid 4 may also be utilized as an ejection port for ejecting fluid from the microchannel. FIGS. 12a through 12d show a cutaway view of a microchannel 3 in which a fluid interface port 17 disposed in a sidewall of the channel can be used as an ejection port. The port 17 forms a virtual wall to allow the ejection of the first liquid 4 from microchannel 3. A suitable ejector 108 is provided in communication with the microchannel to effect ejection of the first liquid through the virtual wall 15. One skilled in the art will recognize that the ejector 108 may comprise any suitable device or system for ejecting a droplet from the microchannel via the virtual wall fluid interface port.

Figure 12A:
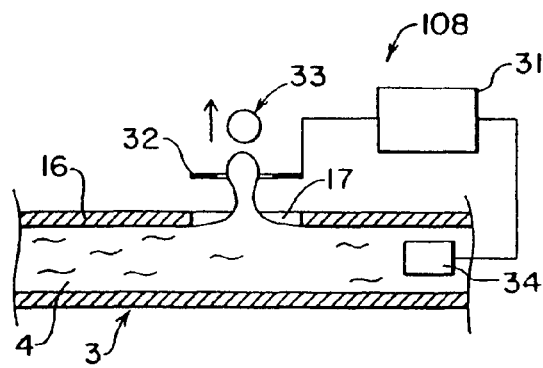
FIG. 12a is a schematic view of one embodiment of the present invention for ejecting liquid from a microchannel through a virtual wall by using electric fields.

According to the illustrated embodiment shown in FIG. 12a, the ejector comprises a first electrode 34 disposed in the first liquid 4 and an electrospray electrode 32 positioned in the vicinity of the port 17. A voltage generator 31 is connected to the first electrode 34 and the electrospray electrode 32 for applying a potential difference and generating an electric field between the electrospray electrode 32 and the first liquid 4. The electric field generated by the voltage generator 31 between the electrodes results in an attractive force on the first liquid 4, thereby effectively pulling the first liquid 4 out of the microchannel through the virtual wall 15 in the form of a droplet 33. The virtual wall and microchannel arrangement shown in FIG. 12a can also be used to receive droplets of a second liquid through the virtual wall, as discussed above, by removing the electric field, thereby achieving a bi-directional interface.

Figure 12B:
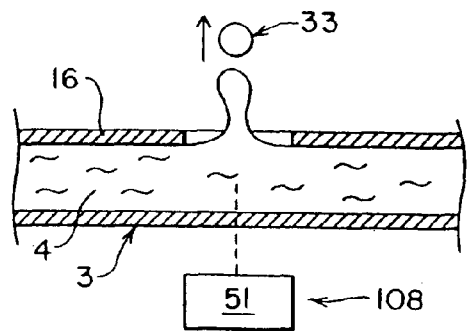
FIG. 12b is a schematic view of an alternate embodiment of the present invention for ejecting liquid from a microchannel through a virtual wall by the application of pressure pulses to the liquid.

FIG. 12b shows another embodiment of the microfluidic system 10 of the present invention suitable for ejecting the first liquid 4 from the microchannel 3. According to this embodiment, the ejector comprises a pressure pulse generator 51 in communication with the first liquid 4 in the microchannel 3. The pressure pulse generator 51 applies a pressure pulse having a selected amplitude, frequency and duration to the fluid 4 to effectively eject the first liquid 4 through the virtual wall to form a droplet 33. The pressure pulse generator 51 can be any suitable structure for generating a pressure pulse within the microchannel 3 and can include a piezoelectric element, an electromagnetic actuator, a heater, an electrostatic actuator, comprising electrodes that move under the influence of an applied voltage, an electrophoretic pressure actuator, comprising electrodes in channel on which a voltage pulse is applied, pressurized gas or any other suitable pressure pulse generator.

The pressure pulse generator 51 can either be integrated at least partly within the microchannel 3 or can be fully external and working with the channel, such as a rod-like moving actuator tapping locally on the channel.

Figure 12C:
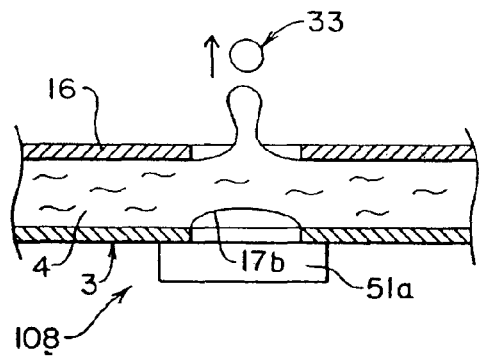
FIG. 12c is a schematic view of still another embodiment of the present invention for ejecting liquid from a microchannel through a virtual wall by the application of a gas pressure pulse to the liquid.

According to another embodiment, shown in FIG. 12c, a gas pressurizer 51a is utilized to eject the liquid from the microchannel. According to the illustrative embodiment, the gas pressurizer 51a comprises a pressurized gas tank, which applies pressure via a fast valve. A second fluid interface port 17b forming a second virtual wall 15b can be formed in the microchannel 3. The second virtual wall 15b is substantially coaxially aligned with the first virtual wall formed in the first fluid interface port 17. The second, coaxial virtual wall 15b is in communication with the gas pressurizer 51a which generates a gas pressure pulse having a selected amplitude, frequency and duration as to effectively eject the first liquid 4 through the first virtual wall 15 in the form of a droplet 33. During the ejection process, the second virtual wall 15b is displaced inwards towards the first liquid 4 so as to form the droplet 33.

Figure 12D:
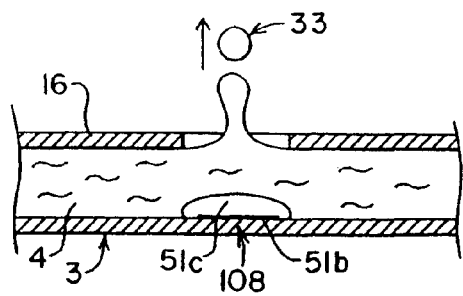
FIG. 12d is a schematic view of yet another embodiment of the present invention for ejecting liquid from a microchannel through a virtual wall by a gas bubble.

According to an alternate embodiment, as shown in FIG. 12d, the ejector comprises a heater 51b disposed in the microchannel 3 along the side wall. The heater 51b locally heats the first liquid 4 in order to form a droplet. The heating of the first liquid results in a quickly growing gas vapor bubble 51c, which effectively ejects the droplet 33 from the microchannel 3 via the virtual wall 15. The heater may comprise a heated spot, an electrical heater, an optically induced heater or any other suitable heater.

According to one embodiment, shown in FIGS. 12e and 12f, the pressure-pulse generator 51 is formed in a holder 500 for a microfluidic chip 10 containing the microchannel 3. The pressure pulse generator can be any suitable device for applying a pressure, such as a piezo-actuated membrane. According to one practice, a membrane 510 is connected to a conical-shaped pressure chamber 511, which is placed opposite the virtual wall 15 and communicates with the microchannel interior. The pressure pulse generator 51 may further include a through-hole 515 formed in the holder and an O-ring 512 for sealing the pressure chamber 511. To eject droplets from the microchannel, as shown in FIG. 12d, an external voltage source applies voltage pulses (typically 500 microseconds/200 V) to form a series of droplets 33 of about ten nanoliters in volume. The illustrative pressure-pulse generator 51 is capable of achieving ejection frequencies of up to 25 Hz, though one skilled in the art will recognize that the invention is not limited to this range. Alterations to the pressure-pulse generator 51 may be made in accordance with the invention. For example, the pressure-pulse generator 51 is not required to form part of chip holder 500 and may be integrated on the microfluidic chip 10 itself.

According to yet another embodiment, shown in FIG. 12g, the ejector 108 comprises a dedicated spotting pin assembly 108 for removing a selected amount of liquid from the microchannel 3 via the fluid interface port 17. The illustrative pin assembly 1080 allows selective removal of sub-nanoliter liquid volumes, though one skilled in the art will recognize that the invention is not limited to this range. According to the embodiment shown in FIG. 12g, the dedicated spotting pin 1080 may comprise a micromachined silicon spotting pin system comprising two pins 1080a and 1080b that are spaced a predetermined distance apart. The space between the pins forms an open capillary 1081, which is dimensioned to accurately pick up predetermined amounts of liquid. To remove a liquid volume from the microchannel 3, the pin is dipped through the port 17 into the microchannel 3. The pin 1080 automatically draws liquid into the capillary 1081 via capillary action. The pin 1080 is then removed from port 17 and the capillary force produced between the surfaces of the pins 1080a and 1080b holds the droplet in the capillary 1081 formed between the two pins 1080a and 1080b. According to the illustrative embodiment, the pin assembly 1080 is able of removing a liquid volume of 300 picoliters from the microchannel, which can be then spotted on a glass slide for further analysis or storage. The illustrative pin assembly 1080 allows a sampling time of about 1 second or less.

A suitable pin assembly 1080 is described in U.S. patent application Ser. No. 10/027,171, filed Dec. 21, 2001 and entitled "Microfabricated Two-Pin Liquid Sample Dispensing System" the contents of which are herein incorporated by reference.

Figure 13A:
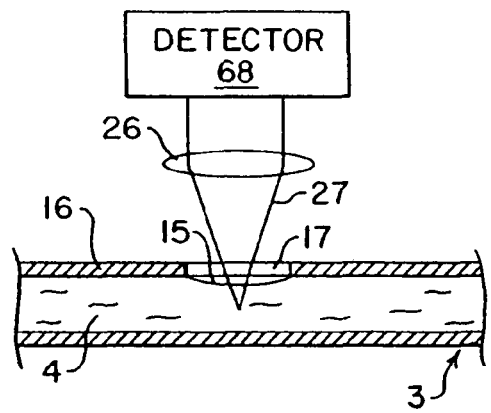
FIG. 13a is a cross-sectional view of a microchannel with a single virtual wall wherein liquid inside the microchannel is optically verified via the virtual wall.

According to yet another embodiment of the invention, the virtual wall 15 formed in the sidewall 16 of the microchannel 3 is utilized to optically analyze the interior of the microchannel. FIG. 13a shows an embodiment of the invention where the first liquid 4 disposed in the microchannel is optically inspected by a light beam 27 focused by an optical element 26. The light beam 27 is co-axially aligned with the fluid interface port 17 in the sidewall as to directly penetrate the first liquid 4 without impinging upon the channel wall 16 opposite the port 17. The optical element 26 can be any suitable lens or prism. A suitable detector 68 is disposed adjacent to the virtual wall 15 to monitor and analyze the liquid in the microchannel 3. In an alternate embodiment, a plurality of fluid interface ports 17 and 17b are at disposed in the side wall at right angles to each other and scattering, rather than absorption, is analyzed.

Figure 13B:
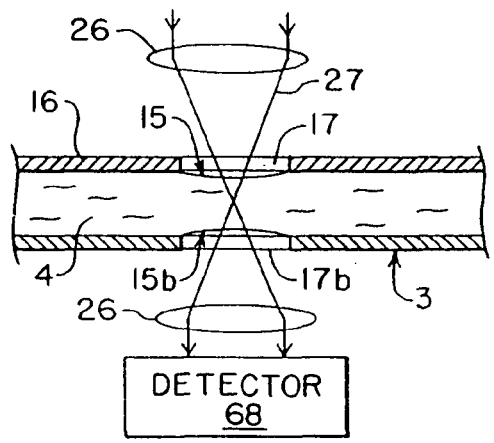
FIG. 13b is a cross-sectional view of a microchannel in which two concentric virtual walls are diametrically opposed, and demonstrates optical detection using both virtual walls.

According to an alternate embodiment for optically analyzing the first liquid 4 through the virtual wall 15, a second virtual wall 15b is disposed in the microchannel 3. FIG. 13b shows an embodiment for optical analysis of first liquid 4 in microchannel 3, in which a first fluid interface port 17 forming a first virtual wall 15 is disposed on one side of the microchannel 3 and a second fluid interface port 17b forming a second virtual wall 15b is disposed on the opposite side of microchannel 3, such that the first virtual wall 15 and the second virtual wall 15b are substantially co-axially arranged. The light beam 27 passing through and focused by the optical element 26 is substantially co-axially positioned relative to the first virtual wall such that the light beam 27 directly penetrates the first liquid 4 through the port 17, and after traveling through the first liquid 4 exits on the opposing side of the microchannel via the second virtual wall 15b. The light passing through the second port 17b can be collected, focused or collimated by a second optical element 26a in communication with an optical detector 68 to monitor and analyze the liquid in the microchannel 3. Such optical detection means are ideally suitable for analyzing liquids containing compounds that are intrinsically colored or fluorescent, or that are labeled with an optically detectable moiety as described elsewhere herein. Alternatively, mass spectrometry may be used as a detection means when a microfluidic chip of the present invention is interfaced with a mass spectrometer.

Figure 14:
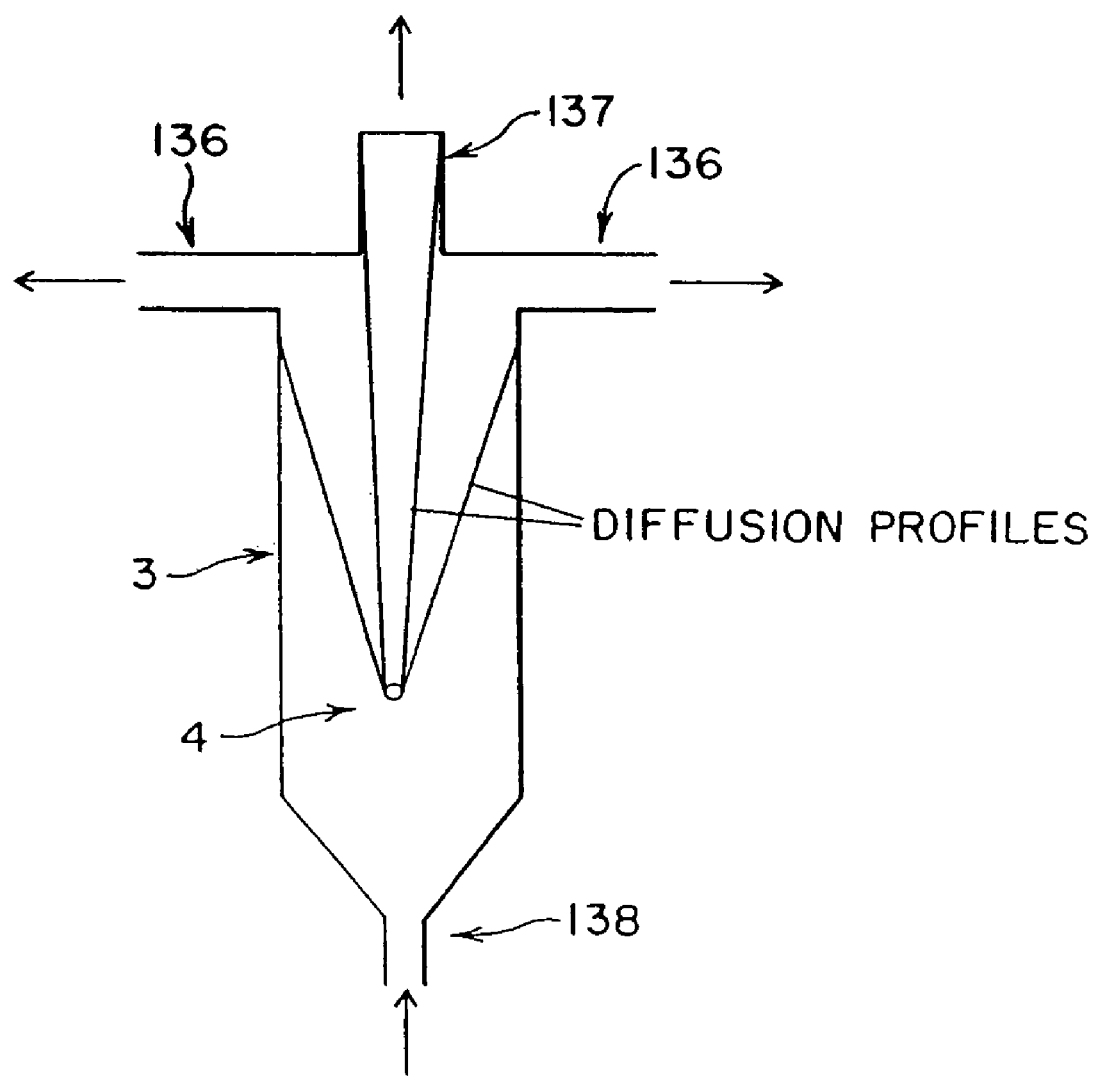
FIG. 14 is a top view of an embodiment of the invention, illustrating the use of a microchannel having a virtual wall to perform a separation.

According to one application of the present invention, a microfluidic system employing an aperture sized and dimensioned to form a virtual wall as a fluid interface port may be utilized to purify or filter a sample. For example, the illustrative arrangement may be utilized to purify a DNA sample by separating contaminants from the DNA fragments in the sample. As shown in FIG. 14, a microchannel 3 having a fluid interface port 17 formed in the sidewall and defining a virtual wall is connected to a plurality of waste channels 136 and an outlet channel 137 formed at the intersection of the waste channels 136 and the microchannel main body 3. The microchannel 3 has an inlet 138 having a smaller diameter than the main body of the microchannel. The microchannel 3 is filled with a suitable washing medium 4 to effect separation of a sample that is introduced via the virtual wall.

To achieve separation of a sample, such as the separation of a DNA sample from contaminants, a fluid flow is induced in the washing medium through the microchannel and the sample is injected into the flowing washing medium via the virtual wall 15. The arrangement exploits diffusion to separate the different components of the sample. The larger molecules (i.e. the DNA fragments) in the sample and the smaller molecules in the sample (i.e. the contaminants) diffuse in the washing medium with different diffusion rates, which effectively separates the different components of the sample according to size. For example, the smaller molecules diffuse into the washing medium faster than the larger molecules. The two sample streams, the residual sample stream containing the larger particles and the diffused sample stream containing the contaminants, are separated into the outlet channel 137 and the waste channels 136, respectively. The purified sample may pass through the outlet channel 137 for further processing, or analysis. The waste channels 136 and the outlet channel 137 may be sized and positioned to receive a selected component. For example, the waste channels 136 are positioned a predetermined distance from the virtual wall 15 to receive the diffused smaller molecules and the outlet channel 137 is sized and positioned to receive the larger molecules.

Alternatively, the configuration shown in FIG. 14 may be utilized to perform chemical manipulations, such as a chemical reaction, non-covalent binding, adsorption or absorption, antibody binding, nucleic acid or oligonucleotide binding or hybridization, ion pairing, ion exchange, chromatographic separation, receptor hormone interaction, enzyme activity antagonism or agonism, or other suitable reaction on an analyte. The present invention applies to a variety of liquid samples, including solutions of compounds, whole cells or cell lysates, enzymes, proteins or peptides, and particles. Accordingly, the invention also has applications in proteomics, genomics, chromatography, diagnostics, and drug discovery.

Alternatively, the illustrative configuration may be utilized to perform a labeling operation, where the virtual wall is utilized as an interface port for one of the reactants in the labeling scheme. According to one embodiment, a labeling operation is performed by running a labeling solution through the microchannel and injecting a liquid containing a substance to be labeled through the virtual wall. Alternatively, the liquid containing the substance to be labeled is conveyed through the microchannel and the labeling solution is injected through a virtual wall to label the substance. The mixing of the two liquids is relatively fast, achieving rapid labeling of the substance. According to one embodiment, the labeling can be performed before a separation step, such as described above. According to one embodiment, a filtration device may also be utilized to remove excess unreacted label after the labeling scheme.

Figure 15A:
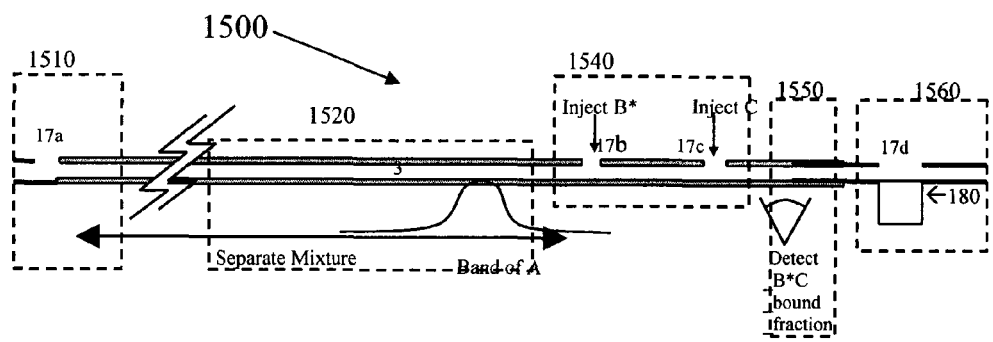
FIG. 15a illustrates a labeling system including a virtual wall formed in a microchannel according to an illustrative embodiment of the invention.

According to another invention, a microfluidic system including a virtual wall fluid interface port also provides a device and method for post-column detection of molecules based on their binding affinity. FIG. 15a illustrates a labeling system 1500 including a plurality of virtual wall fluid interface ports according to another illustrative embodiment of the invention. The labeling system 1500 separates a sample mixture in a column into a plurality of bands, followed by post-column labeling of a band of one unlabeled species in the mixture that comes off the end of a column. The system 1500 may also be used to transfer a labeled band to an analysis system, such as a MALDI-MS and/or multi-well plate based screening assay. As shown the labeling system 1500 includes a channel or separation column 3. The system includes a sample injection region 1510 for injecting a sample or other chemical compound into the channel or column 3 and a separation region 1520 for separating the sample into bands. The system 1500 also includes a second injection region 1540 formed at an end of the channel or separation column 3 for injecting a known amount of a labeled species and/or a binding molecule into the channel or column 3 for labeling one or more of the bands. The system 1500 further includes a detection region 1550 for analyzing and identifying compounds and an ejection region 1560, including an ejector 108 for ejecting selected bands from the channel or column 3 through an ejection port 17*d*.

According to the illustrative embodiment, the injection regions 1510, 1540 include virtual wall interface ports 17*a*, 17*b*, 17*c*, respectively formed in a side wall of the channel or column 3, as described above. Other means of injecting a sample into a column are known in the art and may be used according to the teachings of the invention. The second injection region 1540 may comprise two fluid interface ports 17*b*, 17*c* having virtual walls formed therein are located at the end of the channel or separation column 3, wherein the fluid interface port 17*b* is used to inject the labeled species and the fluid interface port 17*c*, located downstream from the port 17*b*, is used to inject the binding molecule. Droplets of the chemical compound to be injected are formed and propelled towards the aperture 17 and enter the interior of the channel 3 via a meniscus 15 (i.e. a virtual wall) formed by the liquid in the aperture.

The ejector 108 in the ejector region 1560 may comprise any suitable ejector known in the art. Examples of suitable ejectors are described above with respect to FIGS. 12*a*–12*g*. One skilled in the art will recognize that the ejector is not limited to the described embodiments and that any suitable device for ejecting a sample or fraction of a sample from a channel may be used.

Figure 15B:
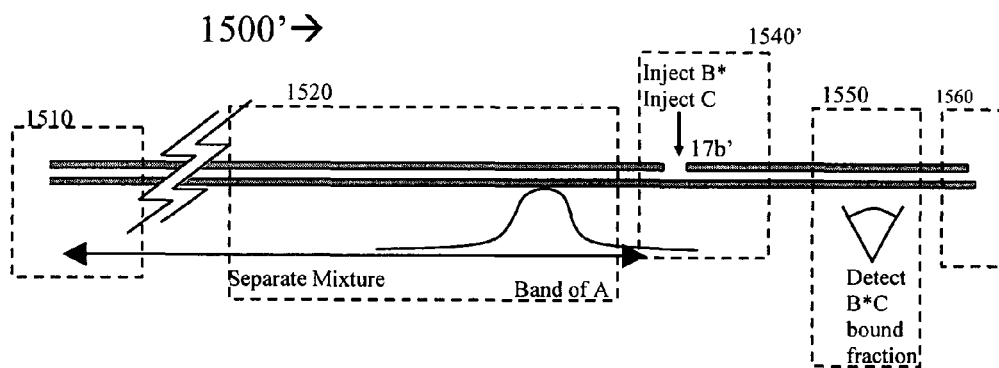
FIG. 15b illustrates a labeling system including a virtual wall formed in a microchannel according to an alternate embodiment.

According to an alternate embodiment, shown in FIG. 15*b*, a labeling system 1500' of an illustrative embodiment of the invention may include a single fluid interface port 17*b*' in the second injection region 1540' to inject the labeled species and binding molecule into the channel or column 3.

Figure 16:
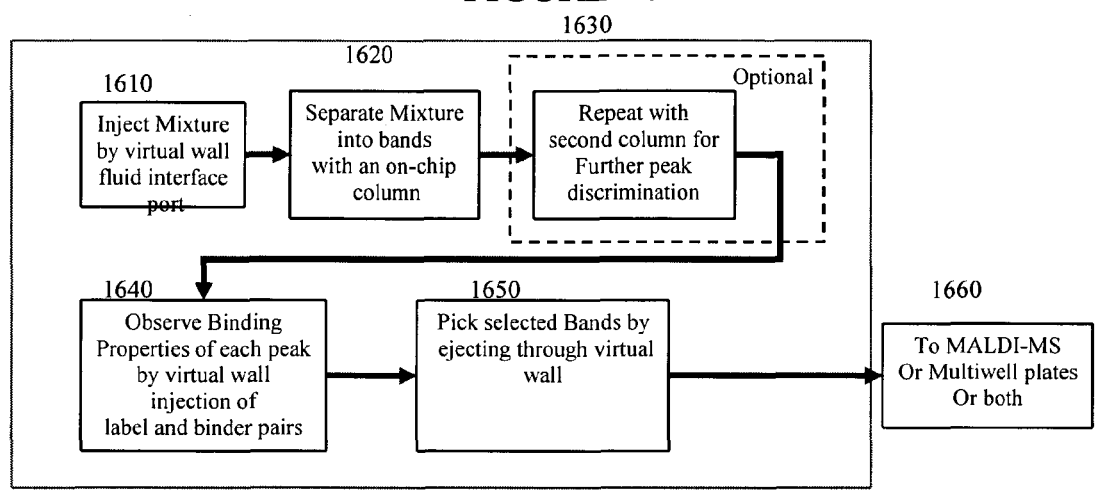
FIG. 16 is a schematic diagram of a labeling operation according to an illustrative embodiment of the invention.

Referring to FIG. 16, an illustrative embodiment of the present invention provides a method of labeling a sample on a microfluidic labeling chip, such as the labeling system of FIGS. 15*a* and 15*b*, comprising at least one column or channel for conveying a sample and other fluids through the chip. In one application, the illustrative method detects a band of an un-labeled species that comes off the end of a column. In step 1610, a sample mixture is injected into a column through a first virtual wall fluid interface port 17*a*, as shown in detail in FIG. 3 or through another suitable injector. In step 1620, the sample mixture is separated into bands with the on-chip column. In an optional step 1630, the step of separating the mixture is repeated in a second column to provide further peak discrimination. In step 1640, the binding properties of each peak (corresponding to a separated band) are observed by injecting label and binder pairs into the column 3 via virtual wall fluid interface ports 17*b* and/or 17*c* (FIG. 15*a*) and/or 17*b*' (FIG. 15*b*). In step 1640, a known amount of a labeled species is injected, followed by a binding molecule, such as an antibody, which binds both the labeled and unlabeled species. The binding molecule equilibrates among the bound states. The resulting binding molecule-labeled molecule complex (B*C) can be identified by (a) having different mobilities in the column so that the bound and unbound bands can be observed downstream from the injection point or (b) giving different Fluorescent Polarization (FP) due to the binding molecule being much larger than the labeled molecule or (c) other methods. In step 1650, selected bands are chosen and ejected from the column using a suitable ejector, as described above. In step 1660, the bands are transferred from to a MALDI-MS system and/or a multi-well plate for further analysis. The illustrative labeling system and method thus provides fast transient measurement of unlabeled molecules based on their binding affinity.

Depending on the particular type of detection method employed, a wide variety of detectable labels may be used in applications of the present invention. Labels are commonly detectable by spectroscopic, photochemical, biochemical, immunochemical, or chemical means. The label is coupled directly or indirectly to a molecule to be detected (a product, substrate, enzyme, or the like) according to methods well known in the art, and for example, as reagents introduced onto a chip via a virtual wall formed in a side wall of a microchannel according to the illustrative embodiment of the present invention. For example, useful nucleic acid labels include fluorescent dyes, enzymes (e.g., as commonly used in an ELISA), biotin, dioxigenin, or haptens and proteins for which antibodies, preferably monoclonal, are available. Other suitable labels include fluorescent moieties, chemiluminescent moieties, magnetic particles, and the like. Still other labeling agents include monoclonal antibodies, polyclonal antibodies, proteins, or other polymers such as affinity matrices, carbohydrates or lipids. Detection of labeled compounds may be by a variety of known methods, including spectrophotometric or optical tracking of fluorescent markers, or other methods which track a molecule based upon size, charge, molecular weight, or affinity. A detectable moiety can be of any material having a detectable physical or chemical property. Such detectable labels have been well-developed in the field of gel electrophoresis, column chromatography, spectroscopic techniques, and the like, and in general, labels useful in such methods can be applied to the present invention. Thus, a label is any composition detectable by spectroscopic, photochemical, biochemical, immunochemical, electrical, optical thermal, or chemical means; and such label may be bound covalently to the molecules of interest (e.g., reaction of amine-containing compounds with ninhydrin) or non-covalently (e.g., reaction of a compound with a labeled antibody). Useful labels in the present invention include fluorescent dyes (e.g., fluorescein isothiocyanate, Texas red, rhodamine, and the like), enzymes (e.g., LacZ, CAT, horse radish peroxidase, alkaline phosphatase and others, commonly used as detectable enzymes, either as marker products or as in an ELISA), nucleic acid intercalators (e.g., ethidium bromide) and colorimetric labels such as colloidal gold or colored glass or plastic (e.g. polystyrene, polypropylene, latex, etc.) beads. Fluorescent labels are particularly preferred labels when optical detection means are employed. Preferred labels are typically characterized by one or more of the following: high sensitivity, high stability, low background, low environmental sensitivity and high specificity in labeling.

Several labels comprising fluorescent moieties are known, including 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthen, 7-hydroxycoumarin, phenoxazine, calicylate, strophanthidin, porphyrins, triarylmethanes and flavin. In some cases, the amino acid tryptophan, which is either part of a peptide or protein of interest (i.e., it is endogenous to that peptide or protein) or which is added to said protein or peptide, may be used as a fluorescent label. Individual fluorescent reagent compounds which may be used in accordance with the invention, or which can be modified to incorporate such functionalities include, e.g., dansyl chloride; fluoresceins such as 3,6-dihydroxy-9-phenylxanthhydrol; rhodamineisothiocyanate; N-phenyl 1-amino-8-sulfonatonaphthalene; N-phenyl 2-amino-6-sulfonatonaphthalene; 4-acetamido-4-isothiocyanato-stilbene-2,2'-disulfonic acid; pyrene-3-sulfonic acid; 2-toluidinonaphthalene-6-sulfonate; N-phenyl-N-methyl-2-aminoaphthalene-6-sulfonate; ethidium bromide; stebrine; auromine-0,2-(9'-anthroyl) palmitate; dansyl phosphatidylethanolamine; N,N'-dioctadecyl oxacarbocyanine: N,N'-dihexyl oxacarbocyanine; merocyanine, 4-(3'pyrenyl)stearate; d-3-aminodesoxy-equilenin; 12-(9'-anthroyl)stearate; 2-methylanthracene; 9-vinylanthracene; 2,2'(vinylene-p-phenylene)bisbenzoxazole; p-bis(2-(4-methyl-5-phenyl-oxazolyl))benzene; 6-dimethylamino-1,2-benzophenazin; retinol; bis(3'-aminopyridinium) 1,10-decandiyl diiodide; sulfonaphthylhydrazone of hellibrienin; chlorotetracycline; N-(7-dimethylamino4-methyl-2-oxo-3-chromenyl)maleimide; N-(p-(2-benzimidazolyl)-phenyl)maleimide; N-(4-fluoranthyl)maleimide; bis(homovanillic acid); resazarin; 4-chloro-7-nitro-2,1,3-benzooxadiazole; merocyanine 540; resorufin; rose bengal; and 2,4-diphenyl-3(2H)-furanone. Many such fluorescent labeling reagents are commercially available from SIGMA chemical company (Saint Louis, Mo.), Molecular Probes, R&D systems (Minneapolis, Minn.), Pharmacia LKB Biotechnology. (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.) as well as other commercial sources known to one of skill in the art.

Fluorescent labels are one preferred class of detectable labels, in part because by irradiating a fluorescent label with light, one can obtain a plurality of emissions. Thus, a single label can provide for a plurality of measurable events. Detectable signal may also be provided by chemiluminescent and bioluminescent sources. Chemiluminescent sources include a compound which becomes electronically excited by a chemical reaction and may then emit light which serves as the detectable signal or donates energy to a fluorescent acceptor. A diverse number of families of compounds have been found to provide chemiluminescence under a variety or conditions. One family of compounds is 2,3-dihydro-1,4-phthalazinedione. The most popular compound is luminol, which is a 5-amino compound. Other members of the family include the 5-amino-6,7,8-trimethoxy- and the dimethylamino[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents. Chemiluminescence may also be obtained with oxalates, usually oxalyl active esters, e.g., p-nitrophenyl and a peroxide, e.g., hydrogen peroxide, under basic conditions. Other useful chemiluminescent compounds are also known and available, including -N-alkyl acridinum esters (basic $H_2O_2$) and dioxetanes. Alternatively, luciferins may be used in conjunction with luciferase or lucigenins to provide bioluminescence. An illustrative example of on-chip labeling with a fluorescent moiety may be found in Harrison, et al., Sensors and Actuators B, vol. 33, pp. 105–09 (1996).

Other labeling moieties may be non-covalently bound to molecules of interest. Generally, a ligand molecule (e.g., biotin) is covalently bound to a polymer. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with labeled, anti-ligands. Alternatively, any haptenic or antigenic compound can be used in combination with an antibody. Labels can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. Means of detecting labels are well known to those of skill in the art. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as digital cameras, charge coupled devices (CCDs) or photomultipliers and phototubes, and the like. Fluorescent labels and detection techniques, particularly microscopy and spectroscopy are preferred. Similarly, enzymatic labels are detected by providing appropriate substrates for the enzyme and detecting the resulting reaction product. Finally, simple colorimetric labels are often detected simply by observing the color associated with the label. For example, conjugated gold often appears pink, while various conjugated beads appear the color of the bead.

Figure 17:
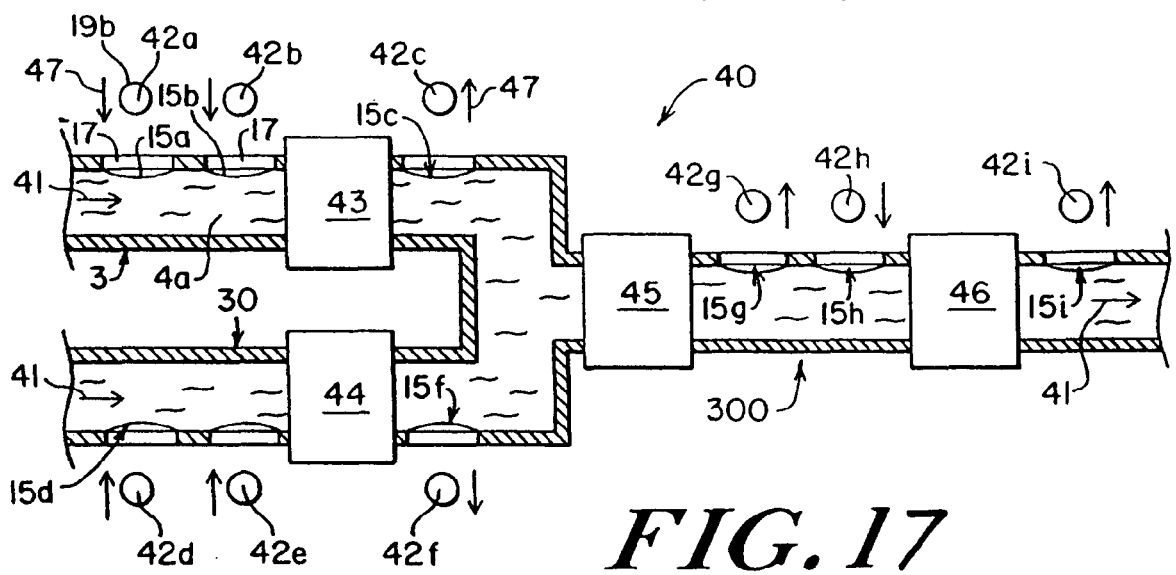
FIG. 17 shows a cutaway view of an embodiment of the invention in which a plurality of virtual walls are employed for performing multi-step chemical experiments.

FIG. 17 illustrates a microfluidic synthesis/analysis system 40 of an embodiment of the present invention for performing a microchemical process of a sample on a chip. The microfluidic synthesis/analysis system 40 comprises a first microchannel 3, a second microchannel 30 operating in parallel with the first microchannel, and a third microchannel 300 disposed at the end of the first and second microchannels and forming an intersection with the first and second microchannels for combining the output of the first microchannel 3 and the second microchannel 30. The microchannels 3, 30 and 300 include a plurality of fluid interface ports 17 forming virtual walls 15*a–i* disposed in the channel side walls for performing a multi-step chemical synthesis or analysis. The illustrative embodiment of the microfluidic synthesis/analysis system 40 serves as an example of the application of virtual walls 15 in microfluidic systems in which complex reaction schemes for synthesis (e.g. labeling, as described above) and analysis are to be performed in a highly parallel fashion. As shown, a large variety of chemical operations can be implemented by using a virtual wall 15 disposed in a sidewall 16 of a microchannel 3.

The illustrated system 40 further includes a plurality of sample processors, illustrated as microreactors 43, 44, 45 and 46, disposed at selected locations in the microchannels 3, 30 and 300 for performing one ore more reactions on a sample, such as a microchemical analysis or synthesis. According to the illustrative embodiment, the illustrated system is utilized to perform a separation of a sample. One skilled in the art will recognize that any suitable process may be performed on a sample, including, but not limited to a reaction, filtration, dilution, mixing, binding and transporting, alone or in combination with other reactions. The specific arrangement shown in FIG. 17 allows performing of the following Reactions 1–4:

Reaction 1: A+B→C
Reaction 2: D+E→F
Reaction 3: C+F→G
Reaction 4: G+H→I

In Reaction 1, substance A (e.g. a labeling reagent) reacts with substance B (e.g., a molecule of interest not otherwise conveniently detectable) to form substance C (e.g a labeled conjugate). In Reaction 2, substance D reacts with substance E to form substance F. In Reaction 3, substances C and F react to form substance G. In Reaction 4, substances G and H react to form substance I. According to the illustrated embodiment, Reaction 1 and Reaction 2 are carried out in parallel, sequentially followed by Reaction 3 and Reaction 4.

In operation, a carrier liquid 4a is disposed in the microfluidic synthesis/analysis system 40 and a number liquids containing a specific chemical substance are interfaced with the carrier liquid 4a via a plurality of virtual walls 15. The reaction products resulting from Reactions 1–4 are carried through the microfluidic synthesis/analysis system by carrier liquid 4a. Droplets 42a–i are formed of liquids respectively containing substances A-I listed in the above reaction scheme. The overall direction of flow of the carrier liquid 4 is indicated by arrows 41. The direction of fluidic interfacing via the virtual walls 15 is indicated by arrows 47.

To initiate the microfluidic process, a first liquid A 42a is introduced into the microfluidic system via a first virtual wall 15a, as indicated by droplet direction 47, and carried through the microchannel by the carrier liquid 4a. A second liquid B 42b is added to the first microchannel 3 through a second virtual wall 15b disposed in the side wall of the microchannel downstream from the first virtual wall 15a, giving rise to a mixture of substances A and B present in carrier liquid 4a. Subsequently, the mixture passes through a first microreactor 43. The first microreactor 43 has appropriate conditions (i.e. temperature, residence time, presence of catalytic materials etc.) to effect Reaction 1 and produce a third substance, liquid C, from the reaction of substances A and B. Liquid C is then carried downstream from the reactor 43 by the carrier liquid 4a. After completion of Reaction 1, portions of liquid C are ejected from the first microchannel 3 through a third virtual wall 15c, disposed downstream of the first and second virtual walls 15a, 15c, in the form of a droplet 42c, as indicated by droplet direction 47. The ejected portion of liquid C may be subsequently stored, further processed or analyzed to determine the composition of the reacted liquid C.

In alternate embodiments of the invention, one or more of the sample processors 43, 44, 45 or 46 may comprise a separation means, rather than a reaction means such as a microreactor. A separation means is typically a chromatography column, preferably a chromatography column. A microfluidic system including a chromatography column may be used to perform a separation of a mixture applied, for example, via virtual wall 17, and then reacted with a labeling reagent in microreactor 45 with a reagent introduced through the virtual wall 15. In such a manner, compounds are labeled post-chromatographic separation. In like manner, a mixture may be introduced though a first virtual wall 15a and a labeling reagent through a second virtual wall 15b, followed by reaction in microreactor and subsequent separation in a chromatography column. Capillary electrophoresis chromatography columns are particularly preferred separation means according to the invention. Such microfluidic CE columns are described in U.S. Pat. Nos. 6,159,353, 5,976,336, and 6,258,263, each of which are incorporated herein by reference. Alternatively, multiple separation means, optionally in parallel, may be employed by the present invention. For example, the microfluidic synthesis/analysis system 40 may perform a first separation by capillary electrophoresis, and another separation based on a pH gradient.

In an alternate embodiment, a titration may be performed on-chip when a color change occurs upon reaction. Such a titration may be, for example, a pH titration, or a titration of an enzyme with a chromogenic substrate or inhibitor.

A similar reaction process to the process that occurs in the first microchannel 3 takes place in the second channel 30 of the microfluidic synthesis/analysis system 40. Respectively, liquid D 42d is introduced in carrier liquid 3b via a fourth virtual wall 15d. Downstream from the injection point for liquid D (i.e. virtual wall 15d), liquid E 42e is injected into the microchannel 3 via a fifth virtual wall 17e to form a mixture of substances D and E in the carrier liquid 4a. Further downstream, the mixture of substances D and E passes through a second microreactor 44, wherein Reaction 2 proceeds. After completion of Reaction 2, a portion of the resulting liquid F can be ejected from the second microchannel 30 via a sixth virtual wall 15f. The ejected portion of liquid F may be subsequently stored, further processed or analyzed to determine the composition of the reacted liquid F.

At the point of intersection of the first microchannel 3 and the second microchannel 30, the liquid C (42c) leaving the first microreactor 43 and the liquid F (42f) leaving the second microreactor 44 mix together and are subsequently carried through the third microchannel 300. The mixture of liquid F and liquid C enters the third microreactor 45, in which Reaction 3 proceeds and produces liquid G. A seventh virtual wall 15g disposed downstream from the third microreactor to allow for portions of liquid G leaving the third microreactor 45 to be ejected from microchannel 3 in the form of liquid droplets 42g. An eighth virtual wall 15h disposed further downstream from the seventh virtual wall liquid 15g is utilized to introduce substance H into the microchannel 300 in the form of liquid droplet 42h, resulting in a mixture of liquid G and liquid H. The G-H mixture enters a fourth microreactor 46, in which Reaction 4 ensues to form liquid I. Finally, portions of the resulting liquid I 42i leaving the fourth microreactor 46 are ejected from the microchannel 3 via a ninth virtual wall 15i disposed in the sidewall of the microchannel 300 for analysis, storage and/or further processing of the liquid I.

According to the illustrative embodiment, the required concentrations of reactants A, B, D, E and H are precisely controlled by metering the size and number of droplets (19b). Moreover, by controlling the number of droplet 19b introduced in carrier liquid 4a, a specific dilution can precisely be obtained allowing the study of reactions 1–4 for different dilutions of reactants A, B, D, E and H. A suitable droplet dispensing system for forming droplets of suitable size is described in Provisional U.S. Patent Application 60/325,040. The use of a direct interface port formed by a virtual wall in the sidewall of the microchannel in the illustrative microfluidic synthesis/analysis system 40 allows precise control over the concentrations of liquids that are introduced into the system and significantly reduces waste while increasing efficiency.

The illustrative embodiment the microfluidic synthesis/analysis system 40 described above serves as an example of the application of a virtual wall 15 in microfluidic systems in which complex reaction schemes for synthesis and analysis are to be performed in a highly parallel fashion. As shown, a large variety of chemical operations can be implemented by using virtual wall 15 disposed in a sidewall of a microchannel. One skilled in the art will recognize that the invention is not limited to the illustrative embodiment and that any suitable size and number of microchannels, virtual walls, reactor types and numbers and sample types may be utilized in accordance with the teachings of the invention.

Figure 18:
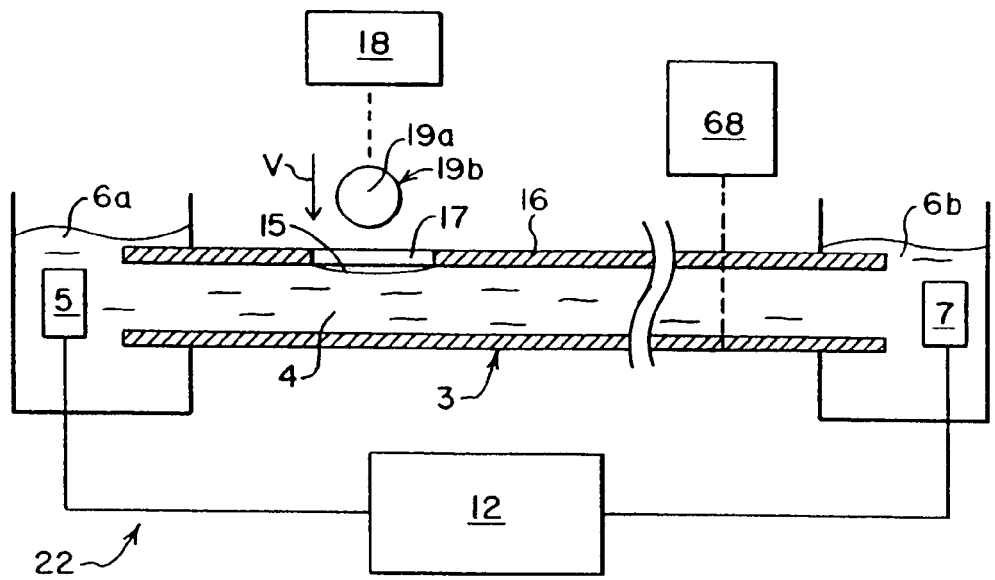
FIG. 18 is a schematic cross-sectional view of an embodiment of the present invention in which a microchannel having a virtual wall part of an electrokinetically operated microfluidic system.

FIG. 18 illustrates an alternate embodiment of the microfluidic system of the present invention. The system 10 includes a microchannel 3 including one or more fluid interface ports forming a virtual wall 15 and comprises a part of an electrokinetically operated system 22. In the electrokinetically operated system 22, an electric field is established to transport fluid through the microchannel 3. As illustrated a first electrode 5 and a second electrode 7 are disposed in or in fluid communication with the first liquid 4 in the microchannel 3. The first electrode 5 is disposed in a first well 6a located at a first end of the microchannel 3 and the second electrode 7 is disposed in a second well 6b located at a second end of the microchannel 3. The first well 6a and the second well 6b are in fluid communication with the first liquid 4 in the microchannel 3. A voltage generator 12 generates a voltage between the first electrode 5 and the second electrode 7, which produces a substantially longitudinal electric field in the first liquid 4 in the microchannel 3. As shown in FIG. 18, the longitudinal electric field is applied by bringing both ends of microchannel 3 in fluidic contact respectively with a first well 4 and a second well 6.

The illustrated port 17 is disposed in the sidewall of the microchannel 3 and forms a virtual wall 15 allowing the introduction of a second liquid into a first liquid 4, according to the teachings of the invention. For example, the droplet generating system 18 forms a droplet 19a of the second fluid 19b. The droplet 19a is directed towards the port 17 via any suitable method, such as those described herein. Depending on the surface properties of the inner walls of the microchannel 3, the longitudinal electric field generated by the electrokinetic system 22 induces an electroosmotic liquid flow of the first liquid 4 in an axial direction through the microchannel 3, thereby substantially transporting the constituents present in the second liquid 19b in the axial direction through the microchannel.

The electrokinetically operated system 22 can include an optional detector 68 to provide for electrophoretic analysis of the constituents present in the second liquid 19b. The opening 17 disposed in the microchannel 3 has suitable properties, such as a selected diameter, length, and inner wall surface properties, to provide electrophoretic separation of the constituents of a liquid. A second liquid 19b to be analyzed is introduced to the microchannel 3 via the virtual wall 15 in the form of a droplet 19a generated by a droplet generating system 18. Constituents present in the introduced second liquid 19b are transported by a combination of electroosmotic flow and migration under the influence of the electric field applied with the voltage generator 12. After traveling a sufficient distance to result in electrophoretic separation of the liquid, the detector 68 detects and analyzes the individual constituents at the end of microchannel 3 by the detector 68. The detector 68 generates an electropherogram from which the composition of second liquid 19a can be determined. Those of ordinary skill will understand that the electrokinetic system of the invention can perform electroosmotic, electrophoretic, and dielectrophoretic techniques.

Figure 19:
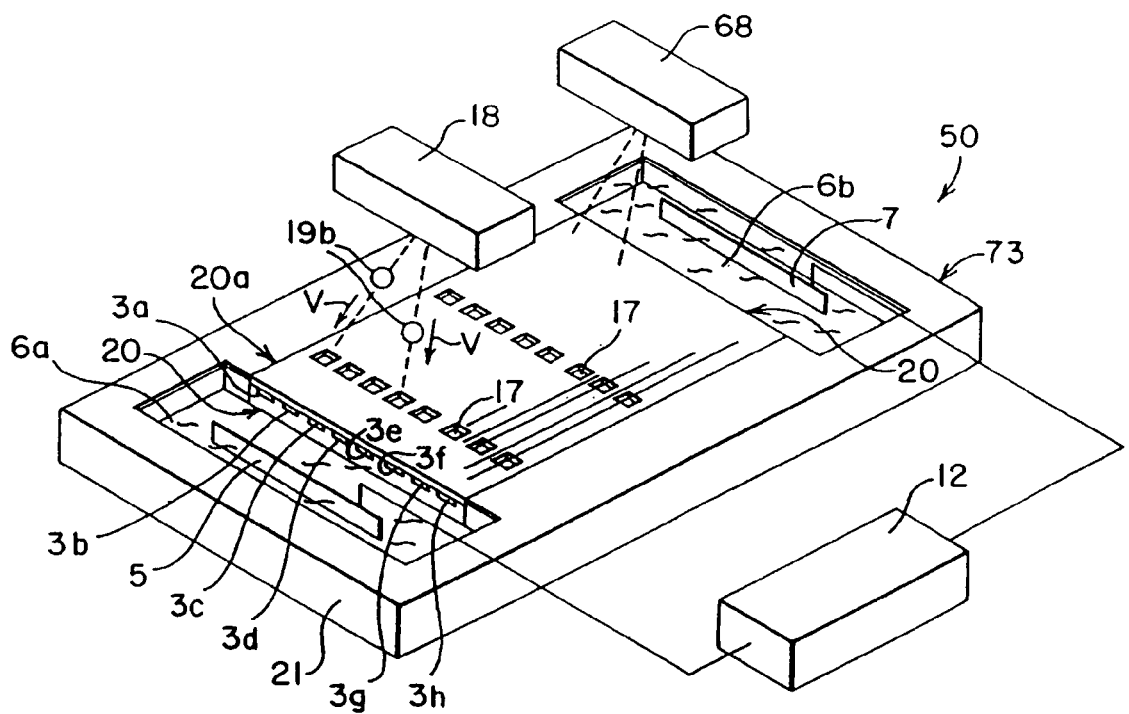
FIG. 19 shows a perspective view of an embodiment according to the invention in which a plurality of microchannels with virtual walls is applied in an electrokinetically operated microfluidic system.

FIG. 19 illustrates another implementation of an electrokinetically operated microfluidic system 50 according to the present invention comprising a plurality of parallel microchannels 3a–3h formed in a cartridge 73 in which a substrate 20 is disposed. The microchannels are formed by forming a network of half-open channel structures in the substrate and covering the half-open channels with a cover 20a to form the plurality of microchannels. The plurality of microchannels 3a–3h are disposed in the substrate in communication with a common first well 6a and a common second well 6b. The microchannels 3a–h include one or more fluid interface ports 17 defined by openings formed in the channel side wall that are sized and dimensioned to form virtual walls when the microchannels are filled with a first liquid 4. A first electrode 5 connected to a voltage generator 12 is disposed in the common first well 6a and a second electrode connected to the voltage generator 12 is disposed in the common second well 6b to establish a substantially longitudinal electric field in the microchannel 3. Droplets 19b are generated by a droplet generator 18. The droplet generator 18 forms and propels the droplets towards a selected virtual wall 15 formed in a fluid interface port form in the side wall of a selected microchannel in a suitable direction and with a suitable velocity to introduce the droplet to the selected microchannel 3 via the opening 17. A detector 68 is positioned relative to the system 50 to monitor and detect the fluid in the microchannels 3a–3h.

In a preferred embodiment, the parallel implementation of an electrokinetically operated system 50 is applied as a highly parallel electrophoretic separation platform, capable of performing a large number of analyses per unit of time. The microchannels 3 disposed in the substrate 20 have suitable properties for electrophoretic separation (inner wall surface properties, diameter and length). The process of electrophoretic analysis of the constituents of droplet 19b is identical as described before. The electrokinetically operated apparatus 50 further includes a detector 68 for detecting and analyzing the individual constituents at the end of microchannels 3. The detector 68 generates an electropherogram from which the composition of second liquid 19a can be determined.

As shown, the illustrative electrokinetically operated system 50 comprises a compact structure, which allows a plurality of different reactions and processes to occur on a relatively small substrate 20. The use of openings forming virtual walls to define fluid interface ports in the side walls of the parallel microchannels 3a–3h allows direct interfacing of fluid with the microchannels, improves injection efficiency and provides easy control over the volume of liquid introduced into the system 50.

Figure 20:
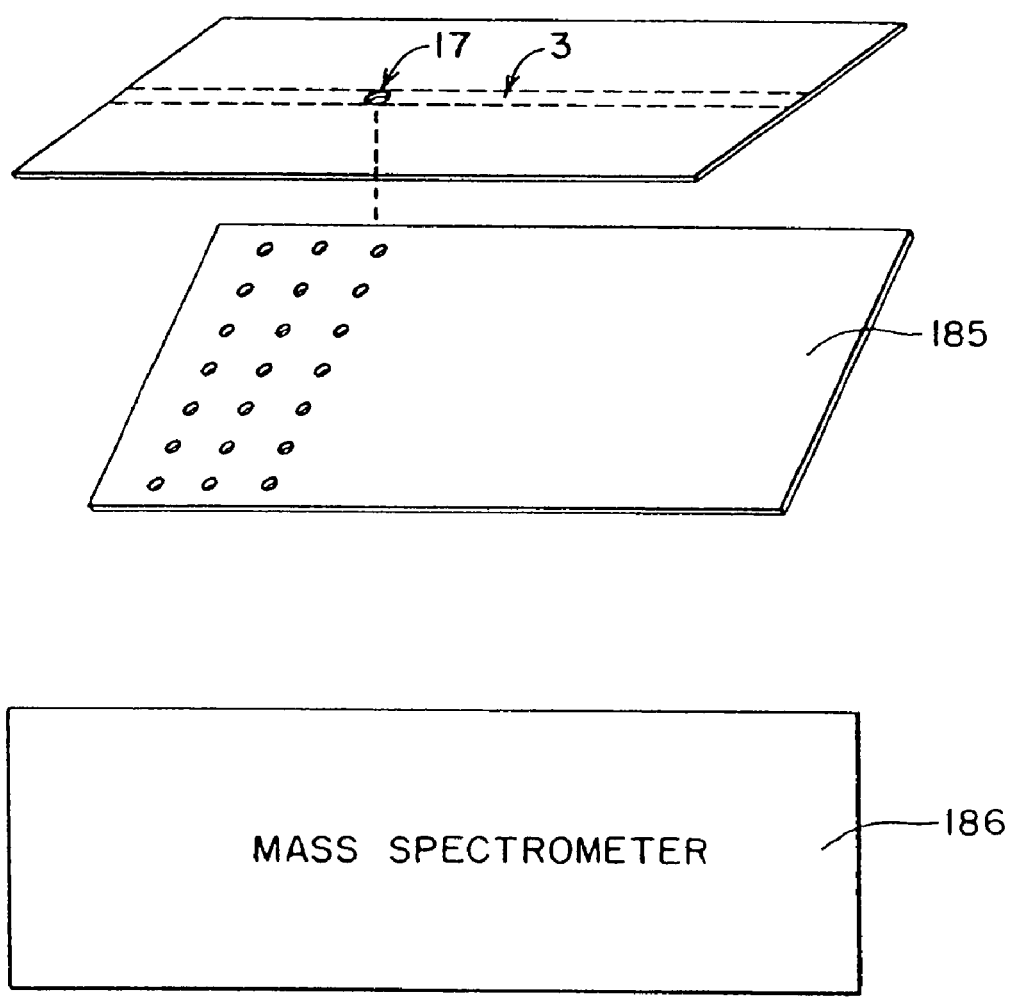
FIG. 20 illustrates an application of the virtual wall interface ports of an illustrative embodiment to interface a microfluidic system with a mass spectrometer.

According to yet another application, the virtual walls may be utilized to interface a microfluidic system 181 with a mass spectrometer, as shown in FIG. 20. For example, a sample may be injected into a microchannel 3 via a virtual wall 15 according to the teachings of the invention and the sample may then be separated into different components. After separation, the different components may be ejected from the microchannel through a virtual wall 15 forming a fluid ejection port in the form of droplets. The droplets may be directed onto a suitable plate 185 for analysis with a mass spectrometer 186 or other robotic system. For example, the microfluidic system 181 may inject the separated samples onto a multi-well plate to form a multi-well array of the sample for analysis.

Figure 21:
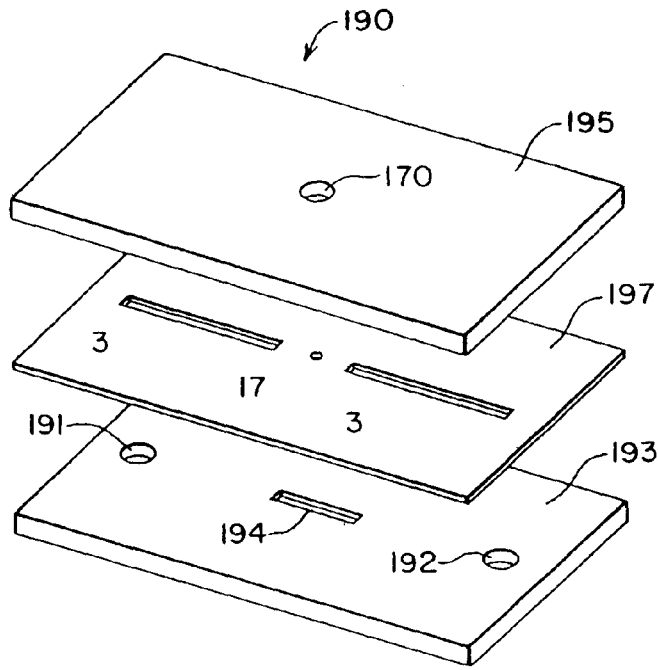
Figure 21:
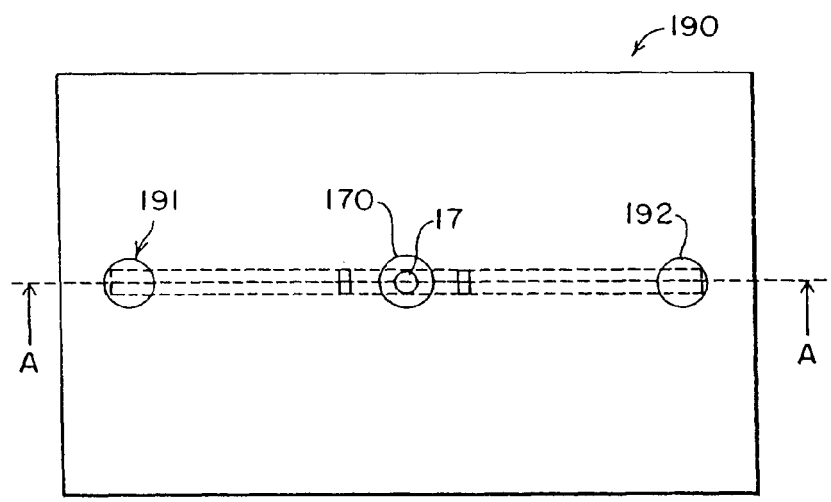
Figure 21:
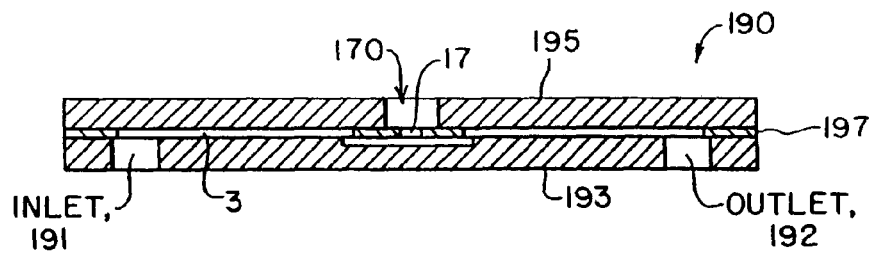

FIGS. 21a, 21b and 21c illustrate a method of manufacturing a microfluidic chip 190 having virtual wall interface ports for processing liquid samples. FIG. 21a is an exploded view of a microfluidic chip 190 employing virtual wall fluid interface ports according to the teachings of the invention. FIG. 21b is a top view of the microfluidic chip 190 of FIG. 21a. FIG. 21c is a cross-sectional side view of the manufactured microfluidic chip 190 of FIG. 21a. As shown, a microchannel 3 with a virtual wall fluid interface ports 17 formed in the side wall of the microchannel may be manufactured with a three-layer "sandwich" construction. As shown, a complete microfluidic chip 190 having a microchannel 3, a first inlet 191 formed at a first end of the microchannel 3, an outlet 192 formed at a second end of the microchannel 3, and a fluid interface port 17 formed in a side wall along the length of the microchannel 3. The microfluidic chip shown in FIGS. 21a–c comprises a first planar sheet 193 having a recess 194 formed therein, a middle layer 197 including a channel 3 and an opening 17 and a second planar sheet 195. The opening 17 has dimensions between about 0.1 μm and about 200 μm and preferably between about 25 μm and about 125 μm and most preferably between about 50 μm and about 100 μm, so that a liquid disposed in the microchannel forms a virtual wall at the opening 17.

To manufacture the microfluidic chip 190, a portion of the first planar sheet 193 is removed to form the recess 194. Next, the middle layer is applied on top of the first sheet. Then, a portion of the middle layer 197 is removed to form the opening 17. Additional portions of the middle layer 197 are removed to form slits defining the microchannel, which are aligned with the recess. The second planar sheet 195 is applied to the middle layer 197, and a virtual wall access hole 170 is formed in the second planar sheet 195 prior to application or after application of the second planar sheet to the middle layer by removing a portion of the second planar sheet. The virtual wall access hole 170 is aligned with the opening 17 formed in the middle layer to provide access to the microchannel. A low temperature bonding process may be utilized to assemble the three layers forming the chip.

According to the illustrative embodiment, the first and second planar sheets 193 and 195 comprise glass plates, though one skilled in the art will recognize that any suitable material may be used. Etching, powderblasting, or any suitable method may form the recess 197, channel 3, inlet 191, outlet 192 and the openings 17 and 170 forming the fluid interface port. According to an alternate embodiment, the recess 197, channel 3, inlet 191, outlet 192 and the openings 17 and 170 may be pre-formed in the layers, i.e. the layers may be molded to form the structures. According to the illustrative embodiment, the middle layer 197 is comprised of a photo patternable material, such as a photosensitive polymer applied by lamination. According to an alternate embodiment, the middle layer 197 of the microfluidic chip 190 also comprises a glass plate.

The use of glass plates to form the microfluidic chip 190 yields better optical detection of the microchannel 3 interior, as the top and bottom of the microchannel are formed by two parallel glass surfaces. In conventional round capillaries and also in etched channels on chip (also partly round surfaces) there is substantial light scattering due to the curved surfaces through which the light should pass. The glass surfaces are very flat and smooth to enhance the flow of fluid through the microchannel 3, and further facilitate and enhance electrophoresis. Furthermore, using glass substrates significantly reduces the cost of manufacturing the microfluidic chip 190.

According to one embodiment, a plurality of microchannels may be formed in the microfluidic chip, and can be configured to intersect with each other.

Figure 22A:
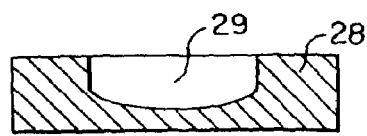
FIGS. 22a–22c illustrate the steps of manufacturing a microchannel having an opening suitable for forming a virtual wall according to an embodiment of the present invention.
Figure 22B:
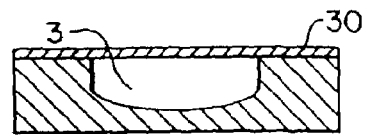
Figure 22C:
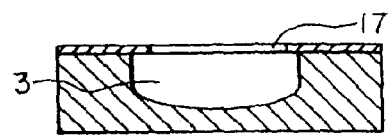

FIGS. 22a–c illustrate the steps of manufacturing a microchannel having a fluid interface port 17 defined by an opening suitable for forming a virtual wall according to an embodiment of the invention. FIG. 22a is a cross-sectional view of a substrate 28 in which a first portion of an open channel 29 is formed. To form an enclosed microchannel, the substrate 28 is then covered with a cover 30, as shown in FIG. 22b. Subsequently, at least a portion of the cover 30 is removed to form the fluid interface port 17 in microchannel 3, as shown in FIG. 22c. As discussed, the fluid interface port 17 is sized and dimensioned to form a virtual wall when the microchannel is filled with a first liquid. In another embodiment the fluid interface port 17 is disposed in the cover 30 prior to bonding the cover 30 on top of substrate 28.

According to the illustrative embodiment, the substrate 30 and the cover 28 are formed of silicon, though one skilled in the art will recognize that any suitable material for forming a microchannel 3 in a microfluidic device or system may be utilized. For example, the microfluidic system may be made out of glass, plastic or any other suitable material. The microchannel 3 may be fabricated from a silicon wafer substrate 30 using a standard photolithography etching process to fabricate the microchannel structures. A photolithography process may also be utilized to etch the fluid interface port 17 in the cover 28. One skilled in the art will recognize that alternative materials and manufacturing techniques, such as wet chemical etching, controlled vapor deposition, laser drilling, and the like, may be utilized.

Figure 23A:
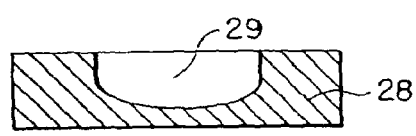
FIGS. 23a–23c illustrate the steps of manufacturing a microchannel with a virtual wall interface port according to another embodiment of the present invention.
Figure 23B:
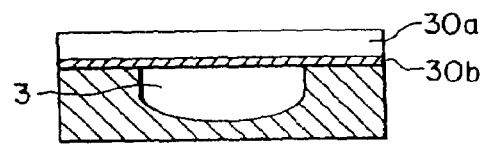
Figure 23C:
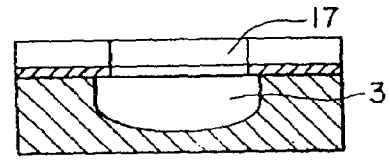

FIGS. 23a–23c illustrate the steps of manufacturing a microchannel with a virtual wall interface port according to another embodiment of the invention. FIG. 23a is a cutaway view of a substrate 28 in which a half open channel structure 29 is disposed. The substrate 28 is then covered with a first cover 30a on which a second cover 30b is disposed, as shown in FIG. 23b to form the enclosed microchannel 3. Subsequently, at least a portion of the first cover 30a and a portion of the second cover 30b are removed as to form the fluid interface port 17 in microchannel 3. As shown, the opening extends through the first cover 30a and the second cover 30b to form a fluidic interface between the interior of the microchannel 3 and the exterior of the microchannel. In another embodiment the fluid interface 17 is formed in first cover 30a and second cover 30b prior to bonding of said first and second cover 30a and 30b to the top of the substrate 28.

According to the illustrative embodiment, the substrate 30 and the first and second covers 30a and 30b are formed of silicon, though one skilled in the art will recognize that any suitable material for forming a microchannel 3 in a microfluidic device or system may be utilized. For example, the microfluidic system may be made out of glass, plastic or any other suitable material. The microchannel 3 may be fabricated from a silicon wafer substrate 30 using a standard photolithography etching process to fabricate the microchannel structures. A photolithography process is utilized to etch the fluid interface port 17 in the first and second covers 30a and 30b. One skilled in the art will recognize that alternative materials and manufacturing techniques, such as wet chemical etching, controlled vapor deposition, laser drilling, and the like, may be utilized.

Figure 24A:
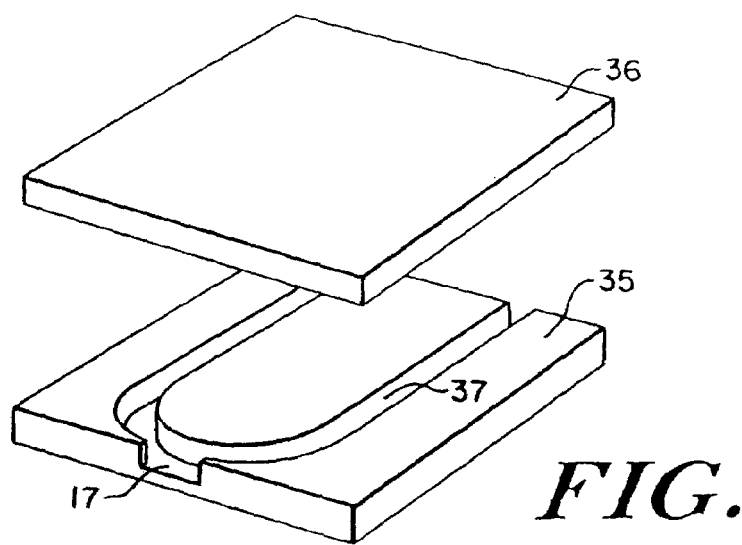
FIGS. 24a–24c illustrate the steps of manufacturing a microchannel having a virtual wall as a fluidic interface port according to an alternate embodiment of the present invention.
Figure 24B:
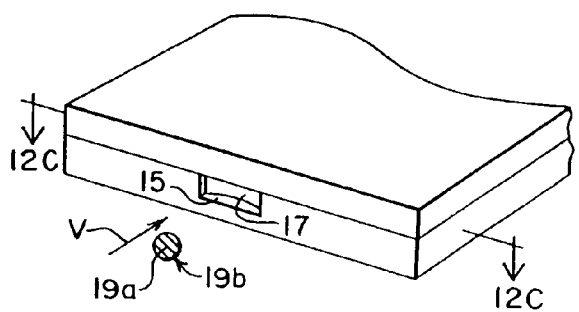
Figure 24C:
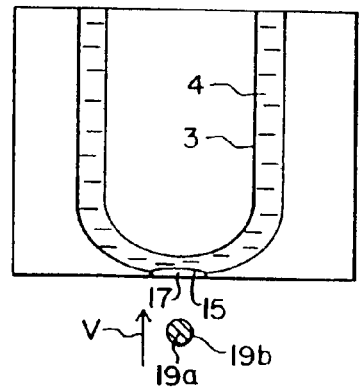

FIGS. 24a–24c illustrate the steps of manufacturing a microchannel having a virtual wall as a fluidic interface port according to an alternate embodiment of the invention. In the embodiment shown in FIGS. 24a–24c, the opening forming the virtual wall is formed in a substrate having a half-open channel structure, rather than a cover for enclosing the half-open channel structure. FIG. 24a shows an exploded view of a substantially planar first cartridge part 35 in which a half open channel structure 37 is disposed. A portion of the side wall of is removed from the half open channel structure 37 in the substrate 35 to form a fluid interface port 17. A second cartridge part 36 is bonded to the top of the first cartridge part 35 to define a microchannel 3.

According to the illustrative embodiment, the first cartridge part 35 and the second cartridge part 36 are formed of silicon, though one skilled in the art will recognize that any suitable material for forming a microchannel 3 in a microfluidic device or system may be utilized. For example, the microfluidic system may be made out of glass, plastic or any other suitable material. The microchannel 3 may be fabricated in the first cartridge part 36 using a standard photolithography etching process. A photolithography process is utilized to etch the fluid interface port 17 in the side wall of the first cartridge part. One skilled in the art will recognize that alternative materials and manufacturing techniques, such as wet chemical etching, controlled vapor deposition, laser drilling, and the like, may be utilized according to the teachings of the present invention.

FIG. 24b and FIG. 24c show respectively a perspective view and a cutaway view of the resulting virtual wall 15 formed in the microchannel. As illustrated, the fluid interface port 17 formed in the microchannel is sized and dimensioned to form a virtual wall at the opening 17 when the microchannel is filled with a first liquid 4. The virtual wall 15 allows fluidic interfacing with the microchannel as described above and is sized and dimensioned to retain liquid within the microchannel without adversely affecting liquid flow through the microchannel. FIGS. 21a and 21c illustrate the introduction of a droplet 19b of a second liquid 19a into a first liquid 4 present in the microchannel 3 via the virtual wall 15 formed within the opening 17. As shown, the droplet is propelled towards the virtual wall and traverses the virtual wall to enter the microchannel.

Figure 25A:
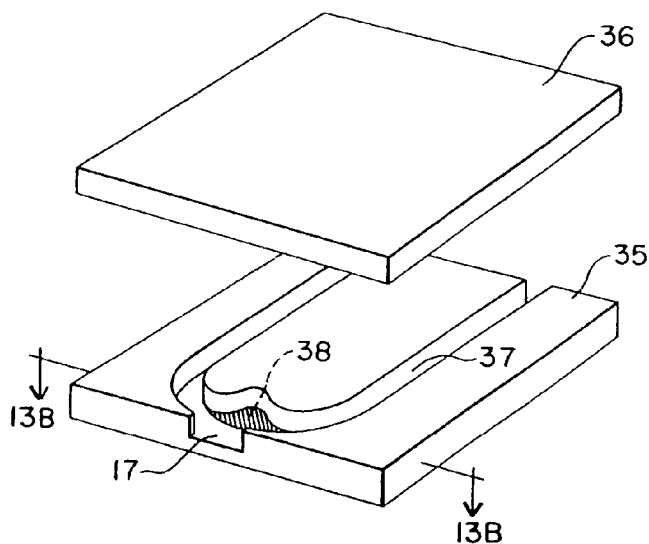
FIG. 25a is a perspective view and of a microchannel with a virtual wall in which a hydrophobic patch is disposed in the microchannel.
Figure 25B:
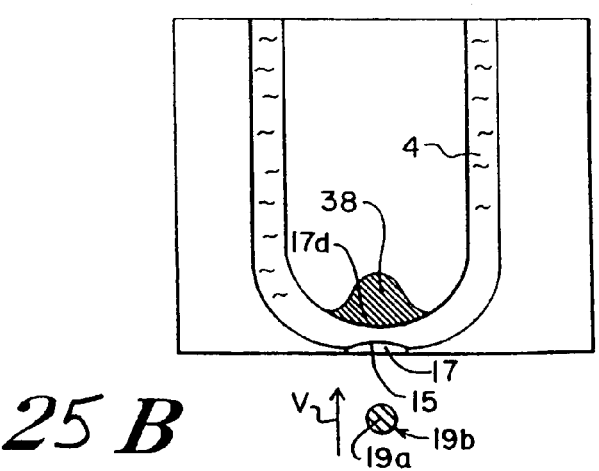

FIGS. 25a and 25b illustrate an alternate embodiment of the microchannel system of FIGS. 21a–21c. FIG. 25a shows an exploded view of a substantially planar first cartridge part 35 in which a half open channel structure 37 is disposed. A portion of the side wall of the cartridge part 35 is removed from the half open channel structure 37 to form an opening 17. A hydrophobic path 38 is disposed substantially opposite the opening 17 in the half open channel structure 37. A second cartridge part 36 is bonded to the top of the first cartridge part to define the microchannel 3. Upon filling of the microchannel 3, a first virtual wall 15 is formed at the opening 17 and a second virtual wall 15a is defined by the hydrophobic patch 38.

The hydrophobic patch enhances introduction of a second liquid into the microchannel. The hydrophobic patch 38 attracts first fluid 4, and prevents escape of the fluid through virtual wall. As illustrated in FIG. 25b, a droplet of a second liquid is introduced into the microchannel via the virtual wall and drawn into the microchannel by the hydrophobic patch.

The use of a virtual wall in a microchannel side wall to create a bi-directional fluid interface for a microfluidic system provides significant advantages over conventional fluid interfaces. The fluid interface port comprising a virtual wall is relatively simple to manufacture, is compact, provides high ejection efficiency, does not adversely affect operation/flow, can be made bi-directional and is useful for a variety of applications. The illustrative embodiment eliminates the need for a separate structure, such as a channel or a reservoir and permits direct injection of a sample into a microchannel.

EXEMPLIFICATION OF THE INVENTION

Example 1

Virtual Wall Microfluidic Chip Manufacturing and Use

Microchannel structures having a fluid interface port were manufactured by isotropic etching half-open channels, 100 micrometer in width, 50 micrometer in height and a length of 20 mm, in a 1.1 mm thick glass wafer. A buffered hydrogen fluoride (HF) solution was used as an etchant and photo patterned etchant resistant silicon nitride mask layers were applied to define the microchannel areas to be etched. Access to the channels was provided by powder blasting 1-mm diameter holes completely through the glass wafer at both ends of each etched half-open microchannel.

A covering 50 micrometer thick layer of dry resist film (LAMINAR® 5000, Shipley, Birkenfeld, Germany) was applied on top of the etched wafer. Fluid interface ports were incorporated by photo patterning circular apertures of 50–150 micrometer in the dry resist film whereby the apertures were aligned with and extended into the underlying microchannels. Finally the wafer was diced in individual chips, which were placed in a holder to connect the microchannel structures to external systems, such as fluid pumps and electric power supplies.

The resulting microchannels were filled with an aqueous buffer solution (50 mM bi-carbonate buffer, pH 9.0). It was observed that the microchannels filled automatically via capillary forces on the application of liquid to the fluid interface port. Liquid drops having a diameter of about 50 micrometer were produced using a piezoelectric-actuated drop dispenser system (MicroDrop GmbH, Norderstedt, Germany). Drops were formed from a buffered solution containing a fluorescent dye (50 mM bi-carbonate buffer, pH 9.0, 1 mM fluoresceine) and were directed to a 100 micrometer diameter interface port. The injection process was monitored using an inverted microscope under UV light irradiation to excite the fluorescent dye and obtain a bright yellow-green color.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense. It is also to be understood that the following claims are to cover all generic and specific features of the invention described herein, and all statements of the scope of the invention which, as a matter of language, might be said to fall therebetween.

What is claimed is:

1. A method of labeling a sample, comprising:
conveying the sample through a channel having a first virtual wall fluid interface port, the first virtual wall fluid interface port comprising a first opening formed in a side wall of the channel, the first opening sized and dimensioned such that a fluid within the channel forms a virtual wall in the first opening to define the first virtual wall fluid interface port;

separating the sample in the channel into a plurality of bands; and injecting a labeling solution through the first virtual wall fluid interface port, wherein the labeling solution interacts with one of said bands to form a labeled band.

2. The method of claim 1, further comprising the step of detecting the labeled band.

3. The method of claim 1, further comprising the step of ejecting at least a portion of the labeled band from the channel.

4. The method of claim 3, wherein the step of ejecting a portion of the labeled band comprises ejecting at least a portion of the labeled band through a second virtual wall interface port in the form of one or more droplets, the second virtual wall fluid interface port comprising a second opening formed in a side wall of the channel, the second opening sized and dimensioned such that a fluid within the channel forms a virtual wall in the second opening to define the second virtual wall fluid interface port.

5. The method of claim 1, wherein the labeling solution comprises a labeled species and a binding molecule for binding to a selected band and the labeled species.

6. The method of claim 5, wherein the step of injecting the labeling solution comprises injecting the labeled species through the first virtual wall fluid interface port and injecting the binding molecule through a second virtual wall fluid interface port, the second virtual wall fluid interface port comprising a second opening formed in a side wall of the channel, the second opening sized and dimensioned such that a fluid within the channel forms a virtual wall in the second opening to define the second virtual wall fluid interface port.

7. The method of claim 1, wherein the virtual wall fluid interface port has a diameter between about 25 μm and about 100 μm, such that when a fluid is disposed in the interior of the channel, the fluid forms a virtual wall at the virtual wall fluid interface port.

8. The method of claim 1, further comprising the step of separating the plurality of bands in to a plurality of sub-bands.

9. The method of claim 1, further comprising the step of transferring a labeled band to one of a MALDI-MS system and a multi-well plate for further analysis.

10. A method of labeling a sample, comprising:

conveying the sample through a channel having a virtual wall fluid interface port, the virtual wall fluid interface port comprising an opening formed in a side wall of the channel, the opening sized and dimensioned such that a fluid within the channel forms a virtual wall in the opening to define the virtual wall fluid interface port; and injecting a labeling solution through the virtual wall fluid interface port, wherein the labeling solution interacts with the sample to label the sample.

11. The method of claim 10, further comprising the step of separating the sample into a plurality of bands.

12. The method of claim 4, wherein the step of ejecting employs a pressure pulse generator, said pressure pulse generator comprising a conical-shaped pressure chamber disposed opposite the second virtual wall fluid interface port and in communication with the interior of the channel and a piezo-actuated membrane connected to the pressure chamber.

13. The method of claim 4, wherein the step of ejecting employs a pin assembly comprising a first pin and a second pin spaced from the first pin to define a capillary for receiving a liquid volume.

* * * * *